(12) United States Patent
Parrag et al.

(10) Patent No.: US 11,464,914 B2
(45) Date of Patent: Oct. 11, 2022

(54) INTRAVITREAL INJECTOR

(71) Applicant: Ripple Therapeutics Corporation, Toronto (CA)

(72) Inventors: Ian Parrag, Toronto (CA); Hans Fischer, Toronto (CA); Dimitra Louka, Toronto (CA); Jared A. Demorat, Toronto (CA); Robert William Henson, Toronto (CA); Eli B. Nichols, Toronto (CA)

(73) Assignee: RIPPLE THERAPEUTICS CORPORATION, Toronto (CA)

( * ) Notice: Subject to any disclaimer, the term of this patent is extended or adjusted under 35 U.S.C. 154(b) by 0 days.

(21) Appl. No.: 16/798,219

(22) Filed: Feb. 21, 2020

(65) Prior Publication Data
US 2021/0113780 A1 Apr. 22, 2021

Related U.S. Application Data

(60) Provisional application No. 62/924,116, filed on Oct. 21, 2019.

(51) Int. Cl.
| | |
|---|---|
| *A61M 5/315* | (2006.01) |
| *A61M 5/31* | (2006.01) |
| *A61M 5/20* | (2006.01) |

(52) U.S. Cl.
CPC ...... *A61M 5/31578* (2013.01); *A61M 5/3148* (2013.01); *A61M 2005/202* (2013.01); *A61M 2205/04* (2013.01); *A61M 2210/0612* (2013.01)

(58) Field of Classification Search
CPC ..... A61F 9/0008; A61M 5/32; A61M 5/3297; A61M 2210/0612; A61M 5/178; A61M 5/3243; A61K 9/0051
See application file for complete search history.

(56) References Cited

U.S. PATENT DOCUMENTS

| | | | | |
|---|---|---|---|---|
| 3,882,863 A | * | 5/1975 | Sarnoff | A61M 5/2033 604/136 |
| 4,086,914 A | * | 5/1978 | Moore | A61M 37/0069 221/4 |
| 4,464,171 A | * | 8/1984 | Garwin | A61M 25/09041 600/435 |
| 4,564,054 A | * | 1/1986 | Gustavsson | A61J 1/2096 141/329 |
| 4,664,654 A | * | 5/1987 | Strauss | A61M 5/326 604/198 |

(Continued)

FOREIGN PATENT DOCUMENTS

| | | |
|---|---|---|
| CA | 2589861 A1 | 6/2006 |
| CA | 2864707 A1 | 8/2013 |

(Continued)

OTHER PUBLICATIONS

PCT/IB2020/000875 International Search Report and Written Opinion dated Jan. 28, 2021.

*Primary Examiner* — Scott J Medway
(74) *Attorney, Agent, or Firm* — Wilson Sonsini Goodrich & Rosati

(57) ABSTRACT

Provided herein are needle assemblies for intravitreal injection of an implant into an eye of a patient through an unsheathed state and a sheathed state. Such needle assemblies are precise and accurate for proper treatment and prevent further damage to the eye.

20 Claims, 31 Drawing Sheets

(56) References Cited

U.S. PATENT DOCUMENTS

| | | | | |
|---|---|---|---|---|
| 4,863,435 A * | 9/1989 | Sturman | A61M 5/3243 | 604/198 |
| 4,897,083 A * | 1/1990 | Martell | A61M 5/3202 | 604/192 |
| 4,950,234 A * | 8/1990 | Fujioka | A61M 37/0069 | 604/60 |
| 4,955,868 A * | 9/1990 | Klein | A61M 5/326 | 604/198 |
| 4,966,592 A * | 10/1990 | Burns | A61M 5/3271 | 604/198 |
| 5,053,010 A * | 10/1991 | McGary | A61M 5/3234 | 604/110 |
| 5,092,851 A * | 3/1992 | Ragner | A61M 5/002 | 604/192 |
| 5,116,326 A * | 5/1992 | Schmidt | A61M 5/3243 | 604/198 |
| 5,269,761 A * | 12/1993 | Stehrenberger | A61M 5/3271 | 604/110 |
| 5,288,291 A * | 2/1994 | Teoh | A61M 37/0069 | 604/218 |
| 5,290,256 A * | 3/1994 | Weatherford | A61M 5/3271 | 604/198 |
| 5,328,483 A * | 7/1994 | Jacoby | A61M 5/282 | 222/213 |
| 5,595,566 A * | 1/1997 | Vallelunga | A61M 5/3243 | 604/110 |
| 5,702,369 A * | 12/1997 | Mercereau | A61M 5/3243 | 604/110 |
| 5,769,822 A * | 6/1998 | McGary | A61M 5/3234 | 604/110 |
| 5,846,225 A * | 12/1998 | Rosengart | A61K 48/00 | 604/115 |
| 6,003,566 A * | 12/1999 | Thibault | A61J 1/2096 | 141/25 |
| 6,378,714 B1 * | 4/2002 | Jansen | A61J 1/1406 | 141/329 |
| 6,478,768 B1 * | 11/2002 | Kneer | A61M 37/0069 | 604/218 |
| 6,776,776 B2 * | 8/2004 | Alchas | A61M 5/3129 | 604/117 |
| 6,899,717 B2 * | 5/2005 | Weber | A61F 9/0017 | 606/107 |
| 7,090,681 B2 * | 8/2006 | Weber | A61F 2/167 | 606/107 |
| 7,300,416 B2 * | 11/2007 | Botich | A61M 5/24 | 604/110 |
| 7,344,517 B2 * | 3/2008 | Schiller | A61M 5/3234 | 604/110 |
| 7,468,065 B2 * | 12/2008 | Weber | A61F 2/167 | 606/107 |
| 7,976,489 B2 * | 7/2011 | Lawter | A61C 19/06 | 604/63 |
| 8,062,252 B2 * | 11/2011 | Alheidt | A61M 5/326 | 604/110 |
| 8,545,554 B2 * | 10/2013 | Novakovic | A61F 2/1662 | 606/107 |
| 8,617,122 B2 * | 12/2013 | Judd | A61M 5/326 | 604/198 |
| 8,932,264 B2 * | 1/2015 | DeSalvo | A61M 5/3243 | 604/187 |
| 8,945,214 B2 * | 2/2015 | Bhagat | A61F 9/0017 | 623/6.12 |
| 9,849,027 B2 * | 12/2017 | Highley | A61F 9/0017 | |
| 2003/0120201 A1 * | 6/2003 | Abergel | A61M 5/19 | 604/28 |
| 2003/0144630 A1 * | 7/2003 | Chang | A61M 5/3272 | 604/198 |
| 2008/0095665 A1 * | 4/2008 | Smith | B01L 3/0279 | 422/400 |
| 2008/0097335 A1 * | 4/2008 | Trogden | A61F 9/0017 | 604/192 |
| 2008/0287913 A1 * | 11/2008 | Schwab | A61M 37/0069 | 604/518 |
| 2009/0118703 A1 * | 5/2009 | Orilla | A61M 5/178 | 604/521 |
| 2010/0152646 A1 * | 6/2010 | Girijavallabhan | A61F 9/007 | 604/22 |
| 2011/0137261 A1 * | 6/2011 | Garber | A61M 5/326 | 604/197 |
| 2011/0190699 A1 * | 8/2011 | Judd | A61M 5/326 | 604/110 |
| 2011/0230844 A1 * | 9/2011 | Shaw | A61M 5/3234 | 604/198 |
| 2012/0215183 A1 * | 8/2012 | Halili | A61M 5/31 | 604/257 |
| 2013/0237910 A1 * | 9/2013 | Shetty | A61M 5/32 | 604/110 |
| 2015/0273161 A1 * | 10/2015 | Bengtsson | A61M 5/001 | 604/198 |
| 2016/0287437 A1 * | 10/2016 | Evans | A61B 5/150656 | |
| 2017/0106135 A1 * | 4/2017 | Bengtsson | A61M 5/001 | |
| 2017/0348486 A1 * | 12/2017 | Andersen | A61M 5/3243 | |
| 2018/0161515 A1 | 6/2018 | Sanders et al. | | |
| 2018/0221584 A1 * | 8/2018 | Grimoldby | A61M 5/3146 | |

FOREIGN PATENT DOCUMENTS

| | | | |
|---|---|---|---|
| CA | 2866212 A1 | 8/2013 | |
| EP | 1666085 A1 | 6/2006 | |
| FR | 2756493 A1 | 6/1998 | |
| WO | WO-2015015127 A2 * | 2/2015 | A61M 25/065 |
| WO | WO-2018091362 A1 | 5/2018 | |
| WO | WO-2019077008 A1 * | 4/2019 | A61M 5/3272 |
| WO | WO-2021079189 A1 | 4/2021 | |

* cited by examiner

INTRAVITREAL INJECTOR

CROSS-REFERENCE

This application claims the benefit of U.S. Provisional Application No. 62/924,116, filed Oct. 21, 2019, which is hereby incorporated by reference in its entirety herein.

BACKGROUND

Ocular injection of solid or particulate medicament must be precise and accurate for proper treatment and prevention of further damage to the eye.

SUMMARY

One aspect provided herein is a needle assembly for injecting an implant into an eye of a patient having an unsheathed state and a sheathed state, the assembly comprising: a needle housing having a proximal end and a distal end; a needle having a proximal end attached to the distal end of the needle housing or within the needle housing, a distal end extending beyond the distal end of the needle housing, and a needle lumen at the distal end of the needle; the implant positioned inside the needle lumen; and a push pin having a head and a push rod, wherein a distal end of the push rod is disposed within the needle lumen, and wherein translating the push pin in a distal direction ejects the implant from the needle lumen and into the eye of the patient.

In some embodiments, the needle assembly further comprises a resilient member disposed within the needle housing. In some embodiments, the resilient member proximally biases the push pin. In some embodiments, the resilient member is a spring, a flexure, a piston, a motor, a band, or any combination thereof. In some embodiments, the needle assembly further comprises a needle sheath having a proximal portion surrounding the distal end of the needle housing, and a distal portion surrounding the distal end of the needle. In some embodiments, the needle sheath is pierced by the needle by translating in a distal direction away from the needle housing to expose the needle. In some embodiments, the needle sheath translates proximally to the unsheathed state where the distal end of the needle extends beyond the distal portion of the needle sheath. In some embodiments, the distal portion of the needle sheath abuts the eye of the patient when the implant is ejected from the needle lumen. In some embodiments, the needle assembly further comprises a needle seal at the distal end of the needle that seals the distal end of the needle lumen. In some embodiments, needle seal is within a distal portion of the needle sheath. In some embodiments, the needle seal is formed of a polymer. In some embodiments, the needle seal is pierced by translating the needle sheath in a proximal direction. In some embodiments, the needle has a length such that the distal end of the needle is within the needle seal when the system is in a sheathed state. In some embodiments, the needle assembly further comprises a removable push pin retainer that prevents movement of the needle housing relative to the needle sheath when engaged. In some embodiments, the removable push pin retainer removably couples the push pin to the needle housing. In some embodiments, the removable push pin retainer removably couples the needle housing to a side wall of the needle sheath. In some embodiments, the implant is loaded in the needle lumen between the distal end of the push pin and the distal end of the needle. In some embodiments, the implant has a shape of elongated cylinder. In some embodiments, the implant comprises a plurality of particles. In some embodiments, the implant has a cross sectional shape of a circle, a triangle, a square, a rectangle, or any other polygon. In some embodiments, the needle has a gauge of 20 to 40. In some embodiments, the needle has a gauge of 20 to 22, 20 to 24, 20 to 26, 20 to 28, 20 to 30, 20 to 32, 20 to 34, 20 to 36, 20 to 38, 20 to 40, 22 to 24, 22 to 26, 22 to 28, 22 to 30, 22 to 32, 22 to 34, 22 to 36, 22 to 38, 22 to 40, 24 to 26, 24 to 28, 24 to 30, 24 to 32, 24 to 34, 24 to 36, 24 to 38, 24 to 40, 26 to 28, 26 to 30, 26 to 32, 26 to 34, 26 to 36, 26 to 38, 26 to 40, 28 to 30, 28 to 32, 28 to 34, 28 to 36, 28 to 38, 28 to 40, 30 to 32, 30 to 34, 30 to 36, 30 to 38, 30 to 40, 32 to 34, 32 to 36, 32 to 38, 32 to 40, 34 to 36, 34 to 38, 34 to 40, 36 to 38, 36 to 40, or 38 to 40. In some embodiments, the needle has a gauge of 20, 22, 24, 26, 28, 30, 32, 34, 36, 38, or 40. In some embodiments, the needle has a gauge of at least 20, 22, 24, 26, 28, 30, 32, 34, 36, or 38. In some embodiments, the needle has a gauge of at most 22, 24, 26, 28, 30, 32, 34, 36, 38, or 40. In some embodiments, the needle has a gauge of 23 to 30. In some embodiments, the needle has a gauge of 23. In some embodiments, the needle has a gauge of 30. In some embodiments, the needle is straight. In some embodiments, the needle is curved.

Another aspect provided herein is an injector system for injecting an implant into an eye of a patient having an unsheathed state and a sheathed state, the system comprising: a plunger assembly comprising: a plunger housing; and a plunger slidably disposed within the plunger housing, wherein a distal end of the plunger engages the push pin of the needle assembly when in a distal position within the plunger housing; and the needle assembly In some embodiments, the distal end of the plunger engages the head of the push pin. In some embodiments, the plunger is manually actuated to translate distally within the plunger housing. In some embodiments, the plunger housing is a syringe barrel. In some embodiments, the syringe barrel is a 1 mL syringe barrel. In some embodiments, the plunger housing is a biopsy punch. In some embodiments, a proximal end of the syringe plunger protrudes beyond the plunger housing. In some embodiments, the plunger is mechanically actuated to translate distally within the plunger housing. In some embodiments, the plunger assembly further comprises a compression spring biasing the plunger towards a proximal end of the plunger housing. In some embodiments, the compression spring has a distal end connected to the plunger housing and a proximal end connected to the plunger. In some embodiments, the plunger comprises a first stop feature, wherein the plunger housing comprises a second stop feature engageable with the first stop feature. In some embodiments, the second stop feature comprises a primary second stop and a retracted second stop.

Another aspect provided herein is an injector system for injecting an implant into an eye of a patient having an unsheathed state and a sheathed state, the system comprising: a plunger assembly comprising: a plunger housing; and a plunger slidably disposed within the plunger housing, wherein a distal end of the plunger engages the push pin of the needle assembly when in a distal position within the plunger housing; and a needle assembly comprising: a needle housing having a proximal end and a distal end; a needle having a proximal end attached to the distal end of the needle housing or within the needle housing, a distal end extending beyond the distal end of the needle housing, and a needle lumen at the distal end of the needle; the implant positioned inside the needle lumen; and a push pin having a head and a push rod, wherein a distal end of the push rod is disposed within the needle lumen, and wherein translating the push pin in a distal direction ejects the implant from the needle lumen and into the eye of the patient.

In some embodiments, the distal end of the plunger engages the head of the push pin. In some embodiments, the plunger is manually actuated to translate distally within the plunger housing. In some embodiments, the plunger housing is a syringe barrel. In some embodiments, the syringe barrel is a 1 mL syringe barrel. In some embodiments, the plunger housing is a biopsy punch. In some embodiments, a proximal end of the syringe plunger protrudes beyond the plunger housing. In some embodiments, the plunger is mechanically actuated to translate distally within the plunger housing. In some embodiments, the plunger assembly further comprises a compression spring biasing the plunger towards a proximal end of the plunger housing. In some embodiments, the compression spring has a distal end connected to the plunger housing and a proximal end connected to the plunger. In some embodiments, the plunger comprises a first stop feature, wherein the plunger housing comprises a second stop feature engageable with the first stop feature. In some embodiments, the second stop feature comprises a primary second stop and a secondary second stop. In some embodiments, the needle assembly further comprises a resilient member disposed within the needle housing. In some embodiments, the resilient member proximally biases the push pin. In some embodiments, the resilient member is a spring, a flexure, a piston, a motor, a band, or any combination thereof. In some embodiments, the needle assembly further comprises a needle sheath having a proximal portion surrounding the distal end of the needle housing, and a distal portion surrounding the distal end of the needle. In some embodiments, the needle sheath is removable from the needle housing by translating in a distal direction away from the needle housing to expose the needle. In some embodiments, the needle sheath translates proximally to the unsheathed state where the distal end of the needle extends beyond the distal portion of the needle sheath. In some embodiments, the distal portion of the needle sheath abuts the eye of the patient when the implant is ejected from the needle lumen. In some embodiments, the injector system further comprises a needle seal at the distal end of the needle that seals the distal end of the needle lumen. In some embodiments, the needle seal is within a distal portion of the needle sheath. In some embodiments, the needle seal is formed of a polymer. In some embodiments, the needle seal is pierced by the needle by translating the needle sheath in a proximal direction. In some embodiments, the needle has a length such that the distal end of the needle is within the needle seal when the system is in a sheathed state. In some embodiments, the needle assembly further comprises a removable push pin retainer that prevents movement of the needle housing relative to the needle sheath when engaged. In some embodiments, the removable push pin retainer removably couples the push pin to the needle housing. In some embodiments, the removable push pin retainer removably couples the needle housing to a side wall of the needle sheath. In some embodiments, the implant is loaded in the needle lumen between the distal end of the push pin and the distal end of the needle. In some embodiments, the implant has a shape of elongated cylinder. In some embodiments, the implant comprises a plurality of particles. In some embodiments, the implant has a cross sectional shape of a circle, a triangle, a square, a rectangle, or any other polygon. In some embodiments, the needle has a gauge of 20 to 40. In some embodiments, the needle has a gauge of 20 to 40. In some embodiments, the needle has a gauge of 20 to 22, 20 to 24, 20 to 26, 20 to 28, 20 to 30, 20 to 32, 20 to 34, 20 to 36, 20 to 38, 20 to 40, 22 to 24, 22 to 26, 22 to 28, 22 to 30, 22 to 32, 22 to 34, 22 to 36, 22 to 38, 22 to 40, 24 to 26, 24 to 28, 24 to 30, 24 to 32, 24 to 34, 24 to 36, 24 to 38, 24 to 40, 26 to 28, 26 to 30, 26 to 32, 26 to 34, 26 to 36, 26 to 38, 26 to 40, 28 to 30, 28 to 32, 28 to 34, 28 to 36, 28 to 38, 28 to 40, 30 to 32, 30 to 34, 30 to 36, 30 to 38, 30 to 40, 32 to 34, 32 to 36, 32 to 38, 32 to 40, 34 to 36, 34 to 38, 34 to 40, 36 to 38, 36 to 40, or 38 to 40. In some embodiments, the needle has a gauge of 20, 22, 24, 26, 28, 30, 32, 34, 36, 38, or 40. In some embodiments, the needle has a gauge of at least 20, 22, 24, 26, 28, 30, 32, 34, 36, or 38. In some embodiments, the needle has a gauge of at most 22, 24, 26, 28, 30, 32, 34, 36, 38, or 40. In some embodiments, the needle has a gauge of 23 to 30. In some embodiments, the needle has a gauge of 23. In some embodiments, the needle has a gauge of 30. In some embodiments, the needle is straight. In some embodiments, the needle is curved.

Another aspect provided herein is an injector system for injecting an implant into an eye of a patient having an unsheathed state and a sheathed state, the system comprising: a needle assembly comprising: a needle housing having a proximal end and a distal end; a needle having a proximal end attached to the distal end of the needle housing or within the needle housing, a distal end extending beyond the distal end of the needle housing, and a needle lumen at the distal end of the needle; the implant positioned inside the needle lumen; and a push pin having a head and a push rod, wherein a distal end of the push rod is disposed within the needle lumen, and wherein translating the push pin in a distal direction ejects the implant from the needle lumen and into the eye of the patient; and a plunger assembly removably coupled to the needle assembly, wherein the plunger assembly comprises: a plunger housing; and a plunger slidably disposed within the plunger housing, wherein a distal end of the plunger engages the push pin of the needle assembly when in a distal position within the plunger housing.

Another aspect provided herein is a method for injecting an implant into an eye of a patient, wherein the method comprises: providing an injector system for injecting an implant into an eye of a patient having an unsheathed state and a sheathed state, the system comprising: a needle assembly comprising: a needle housing having a proximal end and a distal end; a needle having a proximal end attached to the distal end of the needle housing or within the needle housing, a distal end extending beyond the distal end of the needle housing, and a needle lumen at the distal end of the needle; the implant positioned inside the needle lumen; and a push pin having a head and a push rod, wherein a distal end of the push rod is disposed within the needle lumen, and wherein translating the push pin in a distal direction ejects the implant from the needle lumen and into the eye of the patient; and a plunger assembly removably coupled to the needle assembly, wherein the plunger assembly comprises: a plunger housing; and a plunger slidably disposed within the plunger housing; and engaging a distal end of the plunger with the push pin of the needle assembly to inject the implant into the eye of the patient.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

There is currently an unmet need for devices that precisely and accurately intravitreally inject solid or particulate implants. Particularly a device that is simple and intuitive to operate and relies on the clinician-familiar syringe mechanism. Further, there is an unmet need for a device that affords the versatility of employing a variety of needle assemblies based on the implant sizes and/or the needle diameter. Finally, there is a need for a device that is economical to manufacture and whose reusability reduces its environmental impact.

First Injector System

Figure 1:
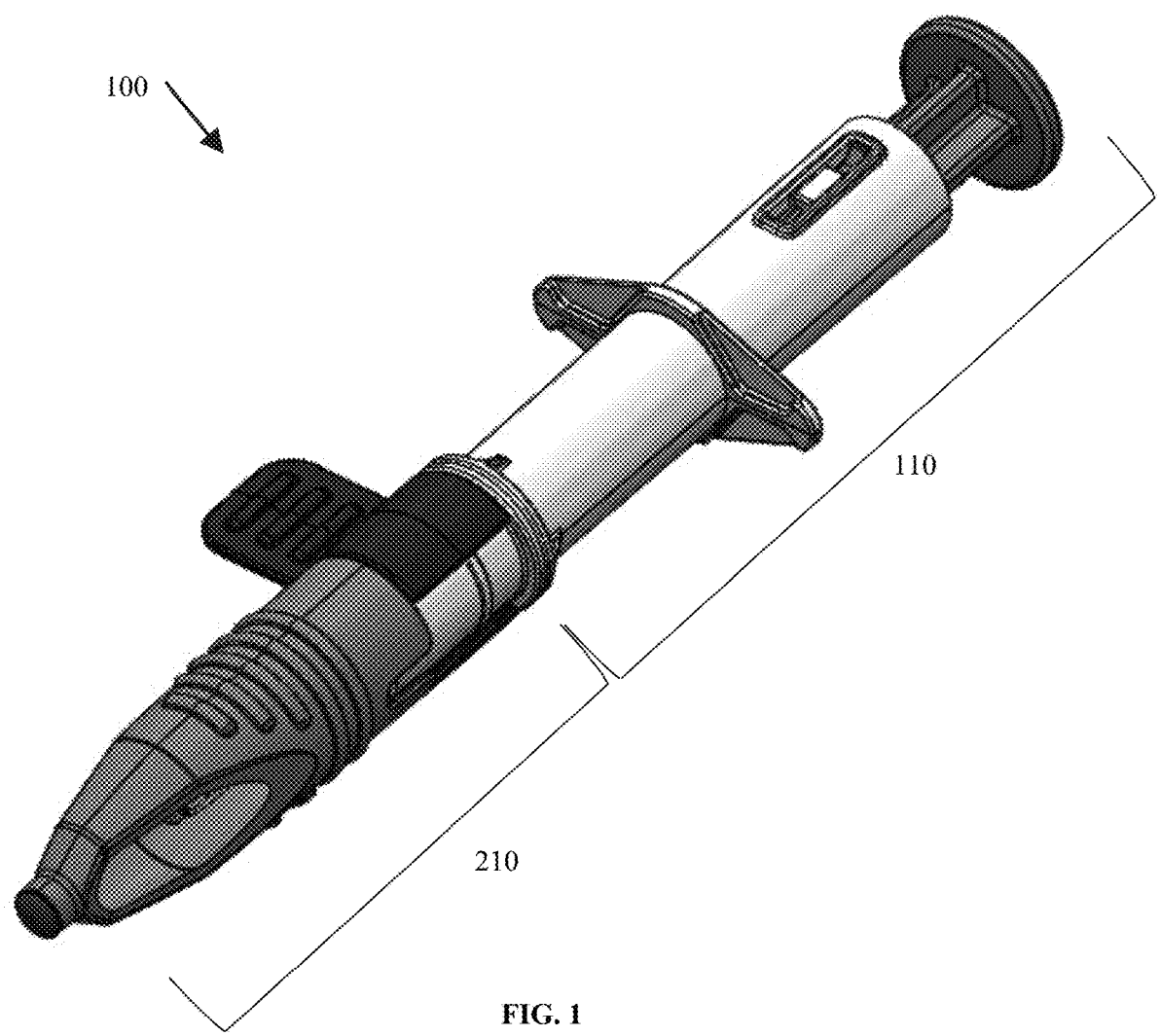
FIG. 1 shows a perspective illustration of an exemplary first injector system in a sheathed state, per some embodiments herein.
Figure 2:
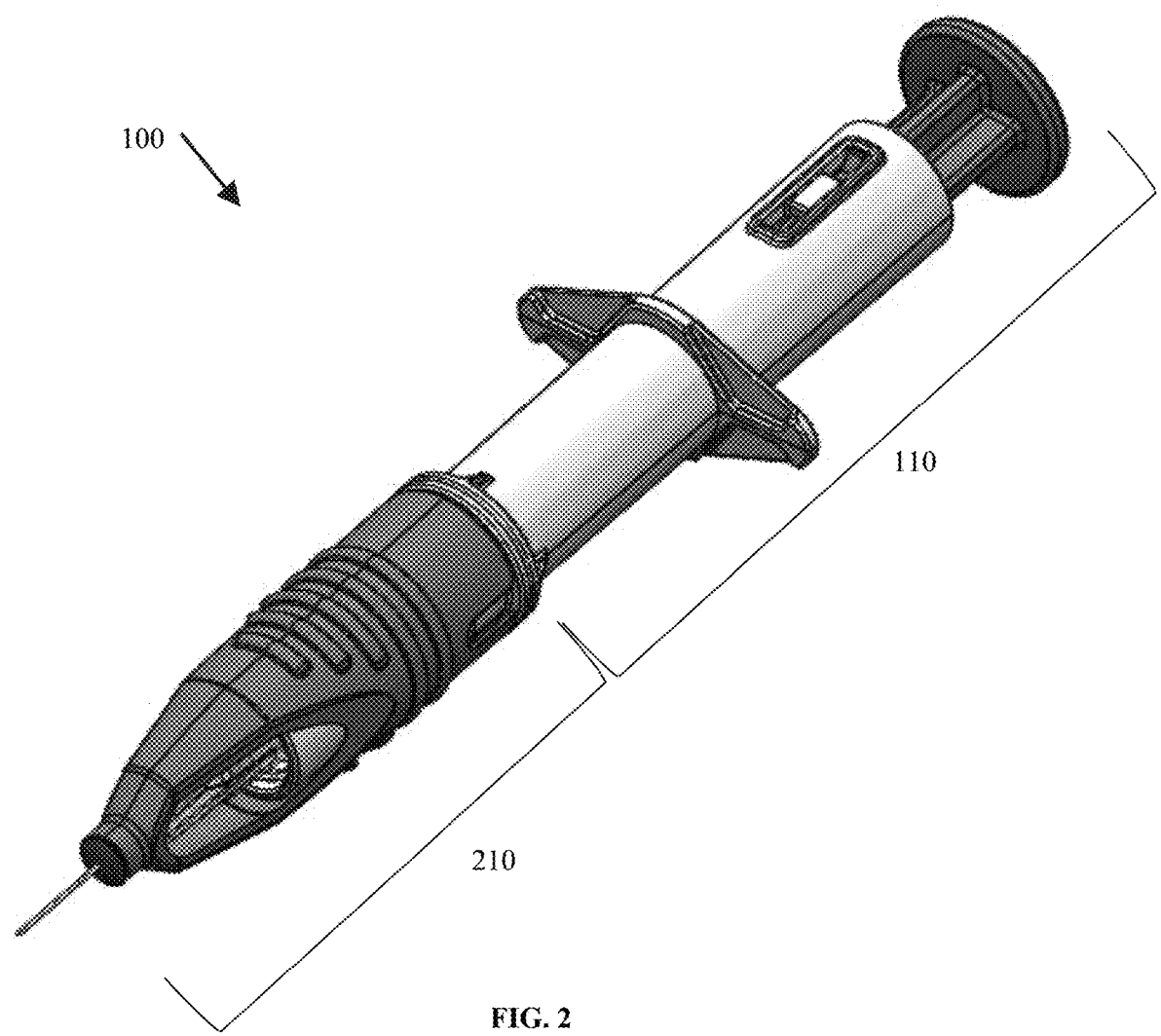
FIG. 2 shows a perspective illustration of an exemplary first injector system in an unsheathed state, per some embodiments herein.
Figure 3:
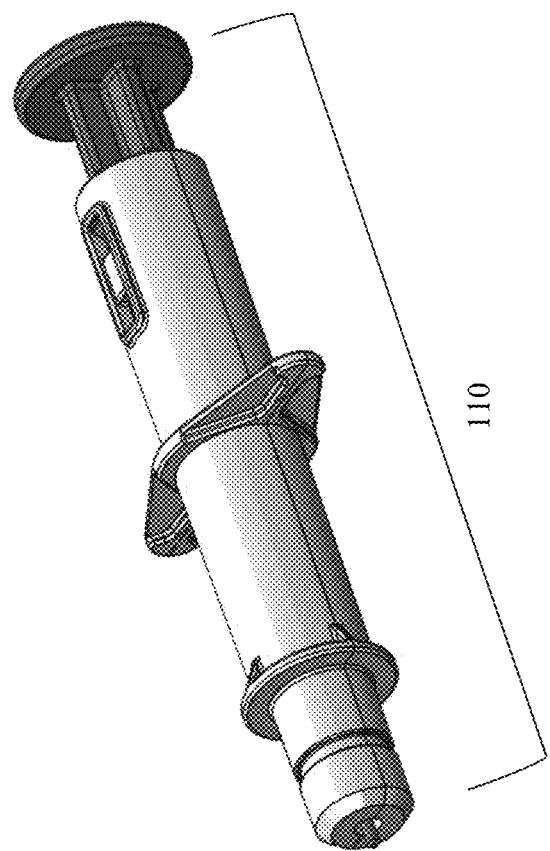
FIG. 3 shows an exploded perspective illustration of an exemplary first injector system, per some embodiments herein.
Figure 3:

Provided herein per FIGS. 1-7 is a first injector system 100 for injecting an implant into an eye of a patient, the system 100 comprising a needle assembly 210 and a plunger assembly 110. As shown in FIG. 3, the needle assembly 210 removably couples to a distal end of the plunger assembly 110. In some embodiments, the needle assembly 210 removably couples to a distal end of the plunger assembly 110 by a snap, a screw, a pin, a band, a clamp, or any combination thereof. Alternatively, in some embodiments, the needle assembly 210 permanently couples to the plunger assembly 110. In some embodiments, the needle assembly 210 is maneuverable between a sheathed state and an unsheathed state. FIG. 1 shows a sheathed state of the needle assembly 210, and FIG. 2 shows an unsheathed state of the needle assembly 210. In some embodiments, the plunger assembly 110 is maneuverable between an extended position and a retracted position.

Figure 4:
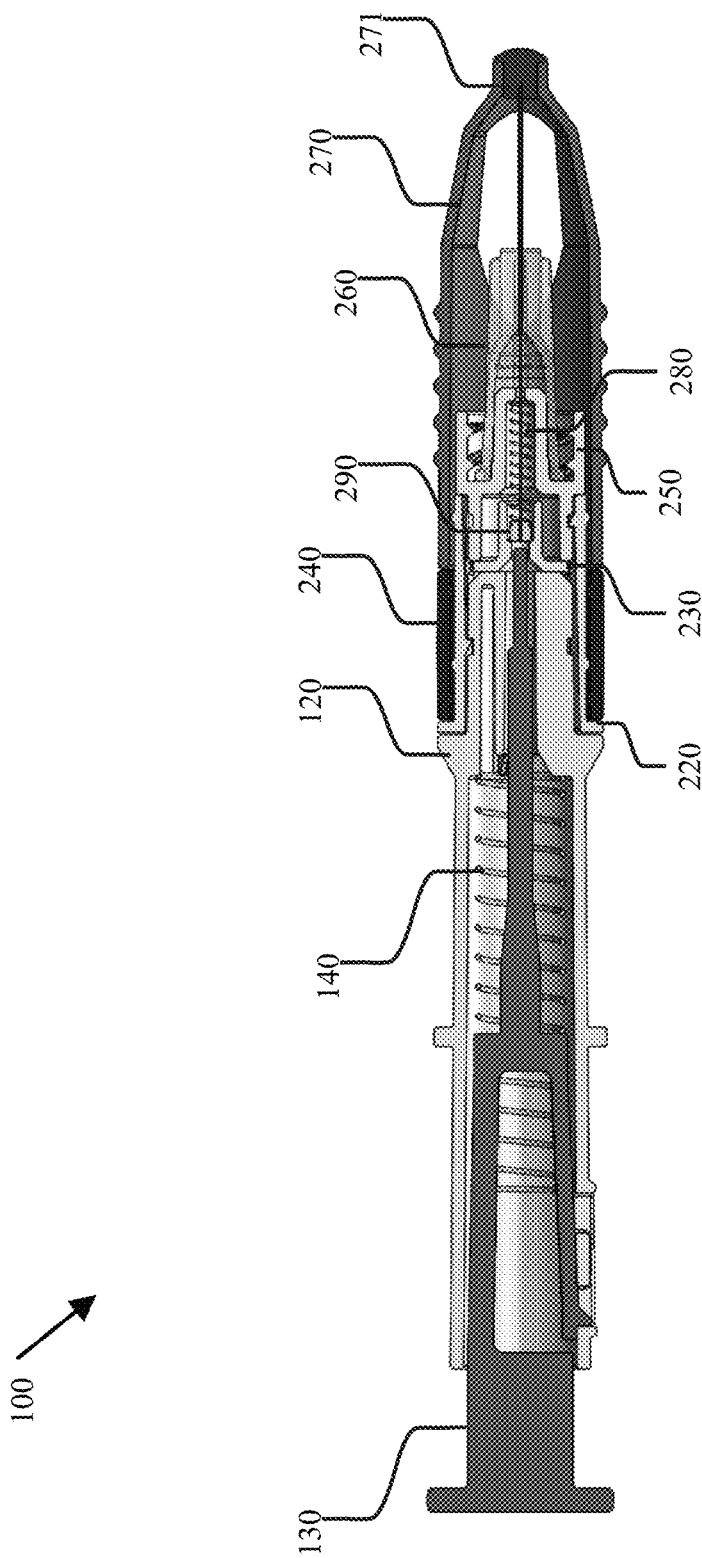
FIG. 4 shows a cross-sectional illustration of an exemplary first injector system in a sheathed state, per some embodiments herein.
Figure 5:
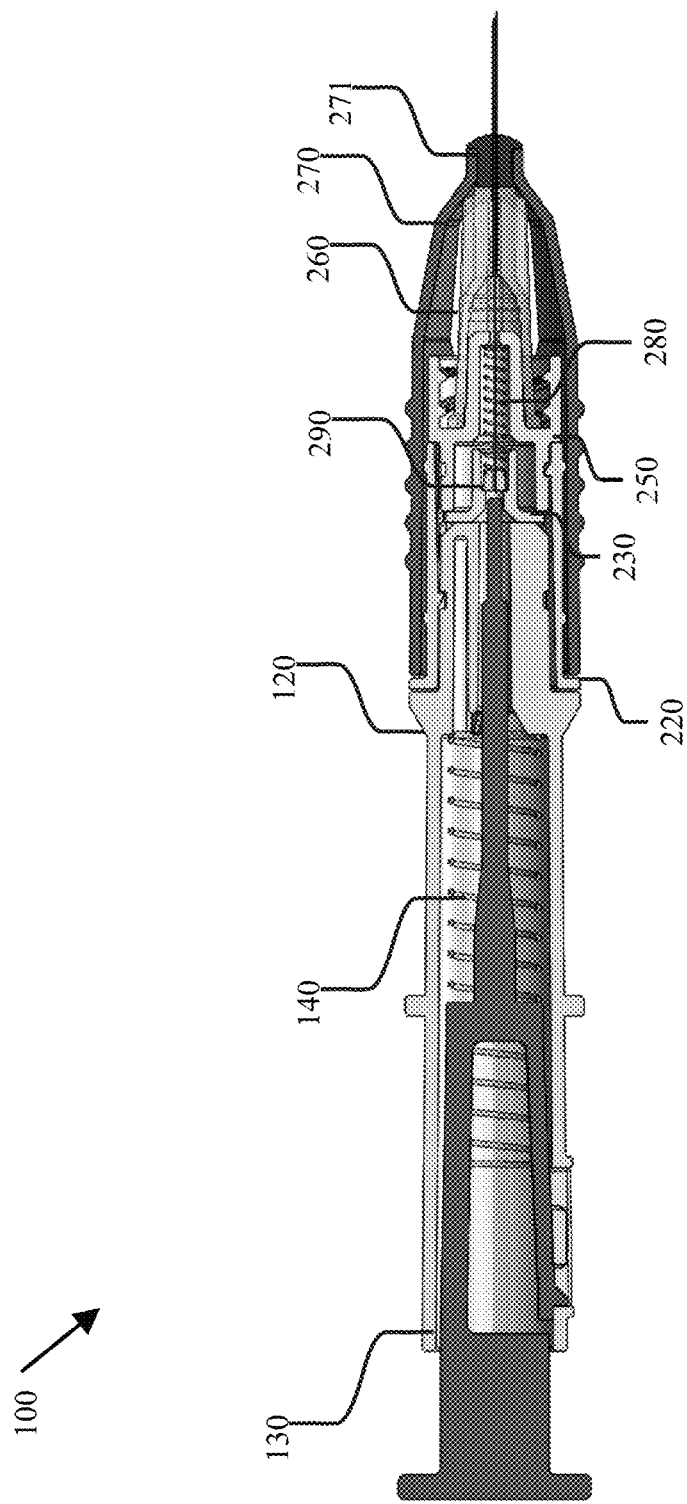
FIG. 5 shows a cross-sectional illustration of an exemplary first injector system in an unsheathed state, per some embodiments herein.
Figure 6:
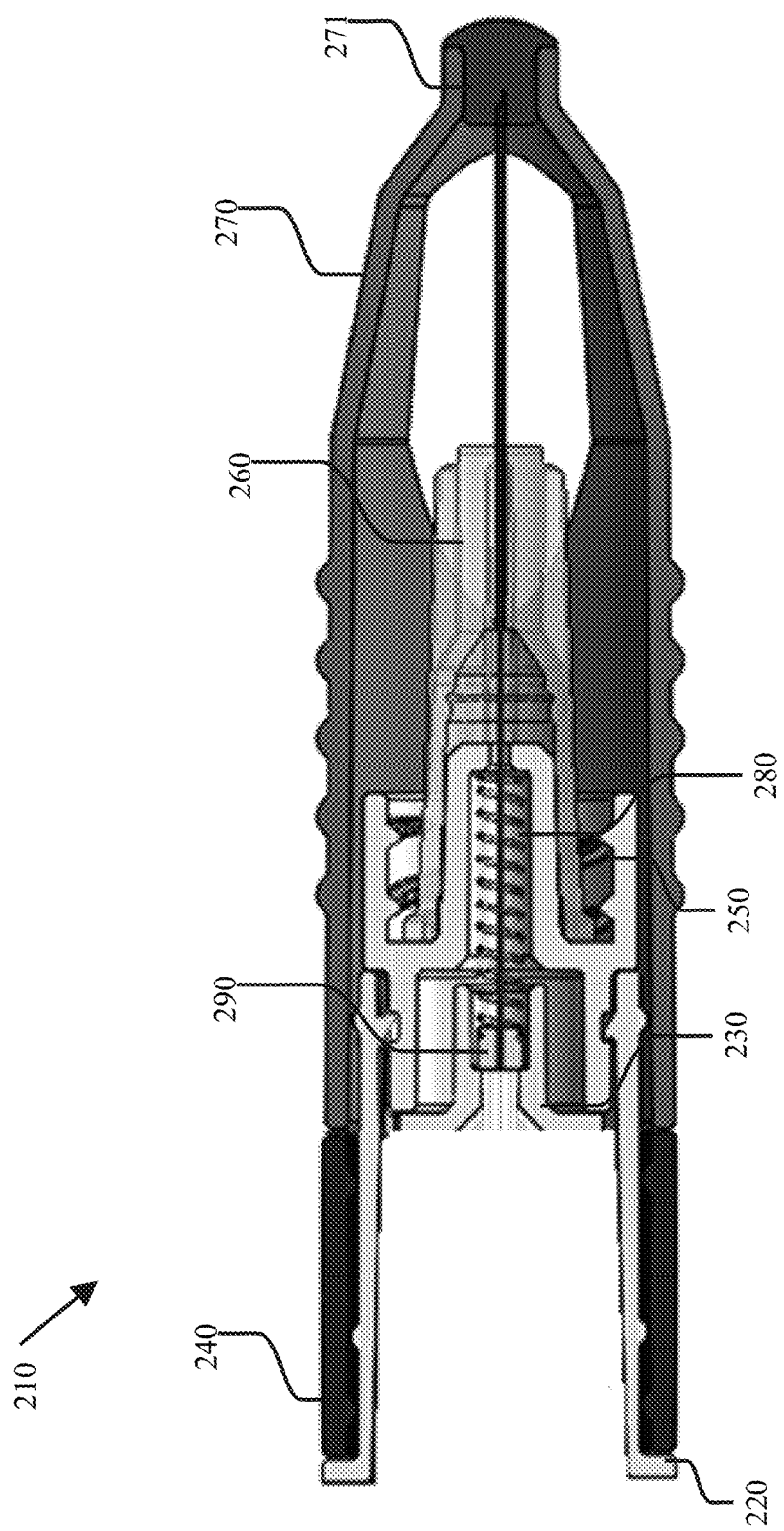
FIG. 6 shows a detailed cross-sectional illustration of a needle assembly of the exemplary first injector system, per some embodiments herein.

As seen per FIGS. 4-6 the exemplary needle assembly 210 comprises a needle housing 250, a needle 260, and a push pin 290. In some embodiments, the needle assembly 210 further comprises the implant loaded in the needle 260. In some embodiments, the needle assembly 210 further comprises the implant loaded in a lumen of the needle 260.

As shown, the needle housing 250 has a proximal end and a distal end. Further, as shown, the needle housing 250 comprises a male luer taper, a thru-hole, a first cavity, and a second cavity. Alternatively, in some embodiments, the needle housing 250 does not comprise one or more of the male luer taper, the thru-hole, the first cavity, and the second cavity. In some embodiments, two or more of the male luer taper, the thru-hole, the first cavity, and the second cavity are concentric. As shown, a distal termination of the first cavity is distal to the distal termination of the male luer taper. As shown, a proximal termination of the first cavity is distal to the distal termination of the male luer taper.

As shown, the needle 260 comprises a needle lumen at the distal end of the needle 260 and a female luer taper at the proximal end of the needle 260. Alternatively, in some embodiments, the needle 260 does not comprise a female luer taper. In some embodiments, the needle 260 has a gauge of 20 to 40. In some embodiments, the needle 260 has a gauge of 20 to 22, 20 to 24, 20 to 26, 20 to 28, 20 to 30, 20 to 32, 20 to 34, 20 to 36, 20 to 38, 20 to 40, 22 to 24, 22 to 26, 22 to 28, 22 to 30, 22 to 32, 22 to 34, 22 to 36, 22 to 38, 22 to 40, 24 to 26, 24 to 28, 24 to 30, 24 to 32, 24 to 34, 24 to 36, 24 to 38, 24 to 40, 26 to 28, 26 to 30, 26 to 32, 26 to 34, 26 to 36, 26 to 38, 26 to 40, 28 to 30, 28 to 32, 28 to 34, 28 to 36, 28 to 38, 28 to 40, 30 to 32, 30 to 34, 30 to 36, 30 to 38, 30 to 40, 32 to 34, 32 to 36, 32 to 38, 32 to 40, 34 to 36, 34 to 38, 34 to 40, 36 to 38, 36 to 40, or 38 to 40. In some embodiments, the needle 260 has a gauge of 20, 22, 24, 26, 28, 30, 32, 34, 36, 38, or 40. In some embodiments, the needle 260 has a gauge of at least 20, 22, 24, 26, 28, 30, 32, 34, 36, or 38. In some embodiments, the needle 260 has a gauge of at most 22, 24, 26, 28, 30, 32, 34, 36, 38, or 40. In some embodiments, the needle 260 has a gauge of 23 to 30. In some embodiments, the needle 260 has a gauge of 23. In some embodiments, the needle 260 has a gauge of 30. In some embodiments, the needle 260 is straight. In some embodiments, the needle 260 is curved. In some embodiments, the curved needle 260 has a curvature radius of about 10, 20, 30, 40, 50, 60, 70, 80, 90 mm or more. In some embodiments, the needle 260 is twisted. In some embodiments, the twisted needle 260 has a pitch of about 5, 10, 15, 20, 25, 30, 35, 40, 45, 50 mm or more. In some embodiments, the twisted needle 260 has a maximum outer diameter of about 5, 10, 15, 20, 25, 30, 35, 40, 45, 50 mm or more. In some embodiments, the needle 260 is a commercially available needle 260.

As shown in FIGS. 4-6 the exemplary push pin 290 has a head and a push rod. Further, as shown, the head is positioned proximally to the push rod. As shown a proximal end of the needle 260 is coupled to the distal end of the needle housing 250 and the push pin 290 is disposed within the needle housing 250. Alternatively, in some embodiments, a proximal end of the needle 260 is within the needle housing 250. As shown, the push rod of the push pin 290 has an outer diameter of less than the inner diameter of the thru-hole of the needle housing 250.

As shown in FIGS. 4-6, the needle assembly 210 further comprises a resilient member 280 disposed within the needle housing 250. In some embodiments, the resilient member 280 proximally biases the push pin 290. In some embodiments, the resilient member 280 proximally biases the push pin 290 when the needle assembly 210 is in a sheathed state. In some embodiments, the resilient member 280 proximally biases the push pin 290 when the needle assembly 210 is in an unsheathed state. As shown, the resilient member 280 is a spring. Alternatively, in some embodiments, the resilient member 280 is a flexure, a piston, a motor, a band, or any combination thereof. In some embodiments, the resilient member 280 is disposed within and constrained by the first cavity of the needle housing 250. In some embodiments, the resilient member 280 has an outer diameter of less than an inner diameter of the first cavity of the needle housing 250. As shown, the push rod of the push pin 290 has an outer diameter of less than an inner diameter of the resilient member 280.

As shown in FIGS. 4-6, the needle assembly 210 further comprises a needle sheath 270 surrounding at least a portion of the needle housing 250, and having a distal portion surrounding the distal end of the needle 260. In some embodiments, a proximal portion of the needle sheath 270 surrounds the distal end of the needle housing 250. In some embodiments, a distal face of the needle sheath 270 is more distal to the needle housing 250 in the sheathed state of the needle assembly 210 than in the unsheathed state of the needle assembly 210. In some embodiments, a distal face of the needle sheath 270 is more distal to the plunger housing 120 in the sheathed state of the needle assembly 210 than in the unsheathed state of the needle assembly 210.

In some embodiments, when the needle assembly 210 is sheathed, the needle 260 is entirely surrounded by the needle sheath 270. In some embodiments, when the needle assembly 210 is in the unsheathed state, at least a portion of the needle 260 extends distally beyond the needle sheath 270. In some embodiments, the distal portion of the needle sheath 270 abuts the eye of the patient when the implant is ejected from the needle lumen. In some embodiments, the distal portion of the needle sheath 270 abuts the eye of the patient when the needle assembly 210 is in its sheathed state. In some embodiments, the distal portion of the needle sheath 270 abuts the eye of the patient when the needle assembly 210 is in its unsheathed state. In some embodiments, the distal portion of the needle sheath 270 abuts the eye of the patient when the needle lumen is within the eye of the patient. In some embodiments, the distal portion of the needle sheath 270 abuts the eye of the patient when the needle lumen is within the needle sheath 270. In some embodiments, the needle sheath 270 is removable from the needle housing 250. In some embodiments, the needle sheath 270 is removable from the needle housing 250 by translation of the needle sheath 270 in a distal direction with respect to the needle housing 250. In some embodiments, the needle sheath 270 is removable from the needle housing 250 by translation of the needle sheath 270 in a proximal direction with respect to the needle housing 250.

As shown in FIGS. 4-6, the first injector system 100 further comprises a needle seal 271 at the distal end of the needle 260 that seals the distal end of the needle lumen. In some embodiments, the needle seal 271 is within a distal portion of the needle sheath 270. In some embodiments, the needle seal 271 is molded within a distal portion of the needle sheath 270. In some embodiments, the needle seal 271 is adhered or coupled to a distal portion of the needle sheath 270. In some embodiments, the needle seal 271 is formed of a polymer. In some embodiments, the polymer is rubber, plastic, or both. In some embodiments, the needle seal 271 is removable. In some embodiments, translating the needle sheath 270 in a proximal direction causes the needle 260 to pierce the needle seal 271.

As shown in FIGS. 4-6, the first injector system 100 further comprises a collar 240, a push pin housing 230, and a collar sleeve 220. Further, as shown the collar sleeve 220 couples to the needle housing 250. As shown some embodiments, the collar sleeve 220 couples to the needle housing 250 by a snap. Alternatively, in some embodiments, the collar sleeve 220 couples to the needle housing 250 via a clip, a magnet, a screw, a bolt, a nut, an adhesive, or any combination thereof. Further, as shown the push pin housing 230 couples to the needle housing 250 by a snap, a clip, a magnet, a screw, a bolt, a nut, an adhesive, or any combination thereof. As shown a distal outer diameter of the push pin housing 230 is less than an inner diameter of the second cavity of the needle housing 250. Also as shown, the push pin housing 230 comprises a chamfered thru-hole receiving a portion of the head of the push pin 290 to maintain alignment of the push pin 290 as it travels distally and proximally. Further, the chamfered thru-hole receives a portion of the distal end of the plunger 130, wherein the chamfer maintains alignment of the distal end of the plunger 130 against the head of the push pin 290. In some embodiments, the plunger 130 comprises a first plunger outer diameter and a second plunger outer diameter distal to the first plunger outer diameter, wherein the second plunger outer diameter is smaller than the first plunger outer diameter. In some embodiments, the first plunger outer diameter is larger than the inner diameter of the chamfered thru-hole in the push pin housing 230. In some embodiments, the second plunger outer diameter is smaller than the inner diameter of the chamfered thru-hole in the push pin housing 230.

As shown, the collar 240 couples to the collar sleeve 220. In some embodiments, the collar 240, when coupled to the collar sleeve 220, prevents the needle sheath 270 from translating in a distal direction, a proximal direction or both. In some embodiments, the collar 240, when decoupled from the collar sleeve 220, allows the needle sheath 270 to translate in a distal direction, a proximal direction or both. In some embodiments, the needle assembly 210 is in a sheathed state, per FIG. 4, when the collar 240 is coupled to the collar sleeve 220. In some embodiments, the needle assembly 210 is in an unsheathed state, per FIG. 5, when the collar 240 is decoupled from the collar sleeve 220. In some embodiments, the collar 240 couples to the collar sleeve 220 by rotating the collar 240, translating the collar 240, or both with respect to the collar sleeve 220. In some embodiments, the collar 240 decouples from the collar sleeve 220 by rotating the collar 240, translating the collar 240, or both with respect to the collar sleeve 220. Further, as shown, the collar 240 comprises a tab to enable rotation of the collar 240, translation of the collar 240, or both with respect to the collar sleeve 220.

As shown in FIGS. 4-6, at least one of the push pin 290, the needle housing 250 and the needle 260 is dimensioned such that translating the push pin 290 in a distal direction ejects the implant positioned inside the needle lumen out of the needle lumen and into the eye of the patient. In some embodiments, at least one of the push pin 290, the needle housing 250 and the needle 260 is dimensioned such that translating the push pin 290 in a distal direction partially ejects the implant out of the needle lumen. In some embodiments, at least one of the push pin 290, the needle housing 250 and the needle 260 is dimensioned such that translating the push pin 290 in a distal direction completely ejects the implant out of the needle lumen. In some embodiments, at least one of the push pin 290, the needle housing 250 and the needle 260 is dimensioned such that translating the push pin 290 in a distal direction completely ejects the implant out of the needle lumen by about 1, 2, 3, 4, 5, 6, 7, 8, 9, or 10 mm. In some embodiments, at least one of the push pin 290, the needle housing 250 and the needle 260 is dimensioned such that translating the push pin 290 in a distal direction completely ejects the implant out of the needle lumen by at least about 1, 2, 3, 4, 5, 6, 7, 8, 9, or 10 mm. In some embodiments, at least one of the push pin 290, the needle housing 250 and the needle 260 is dimensioned such that translating the push pin 290 in a distal direction completely ejects the implant out of the needle lumen by at most about 1, 2, 3, 4, 5, 6, 7, 8, 9, or 10 mm.

In some embodiments, at least one of the push pin 290, the needle housing 250, and the needle 260 is dimensioned such that translating the push pin 290 in a distal direction positions a distal end of the push rod of the push pin 290 distal to the distal end of the needle 260. In some embodiments, at least one of the push pin 290, the needle housing 250, and the needle 260 is dimensioned such that translating the push pin 290 in a distal direction positions a distal end of the push rod of the push pin 290 distal to the distal end of the needle 260 by about 1, 2, 3, 4, 5, 6, 7, 8, 9, or 10 mm. In some embodiments, at least one of the push pin 290, the needle housing 250, and the needle 260 is dimensioned such that translating the push pin 290 in a distal direction positions a distal end of the push rod of the push pin 290 distal to the distal end of the needle 260 by at least about 1, 2, 3, 4, 5, 6, 7, 8, 9, or 10 mm. In some embodiments, at least one of the push pin 290, the needle housing 250, and the needle 260 is dimensioned such that translating the push pin 290 in a distal direction positions a distal end of the push rod of the push pin 290 distal to the distal end of the needle 260 by at most about 1, 2, 3, 4, 5, 6, 7, 8, 9, or 10 mm. In some embodiments, at least one of the push pin 290, the needle housing 250 and the needle 260 is dimensioned such that translating the push pin 290 in a distal direction positions a distal end of the push rod of the push pin 290 proximal to the distal end of the needle 260. In some embodiments, at least one of the push pin 290, the needle housing 250 and the needle 260 is dimensioned such that translating the push pin 290 in a distal direction positions a distal end of the push rod of the push pin 290 proximal to the distal end of the needle 260 by about 1, 2, 3, 4, 5, 6, 7, 8, 9, or 10 mm. In some embodiments, at least one of the push pin 290, the needle housing 250 and the needle 260 is dimensioned such that translating the push pin 290 in a distal direction positions a distal end of the push rod of the push pin 290 proximal to the distal end of the needle 260 by at least about 1, 2, 3, 4, 5, 6, 7, 8, 9, or 10 mm. In some embodiments, at least one of the push pin 290, the needle housing 250 and the needle 260 is dimensioned such that translating the push pin 290 in a distal direction positions a distal end of the push rod of the push pin 290 proximal to the distal end of the needle 260 by at most about 1, 2, 3, 4, 5, 6, 7, 8, 9, or 10 mm.

In some embodiments, at least one of the push pin 290, the needle housing 250, or the needle 260 is dimensioned such that applying an actuating force on the push pin 290 in a distal direction positions a distal end of the push rod of the push pin 290 distal to the distal end of the needle 260. In some embodiments, the push pin 290 retracts within the needle 260 after the actuating force is removed. In some embodiments, the push pin 290 retracts within the needle 260 by a distance of at least about 1, 2, 3, 4, 5, 6, 7, 8, 9, or 10 mm. In some embodiments, the push pin 290 retracts within the needle 260 by a distance of at most about 1, 2, 3, 4, 5, 6, 7, 8, 9, or 10 mm. In some embodiments, the push pin 290 retracts within the needle 260 by a distance of 1, 2, 3, 4, 5, 6, 7, 8, 9, or 10 mm from the distal face of the needle 260 after the actuating force is removed.

In some embodiments, the needle 260 has a length such that the distal end of the needle 260 is within the needle seal when the needle assembly 210 is in a sheathed state. Further, as shown, at least a portion of the push rod of the push pin 290 is disposed within the needle 260, and at least a portion of the push pin 290 is disposed within the needle housing 250. As shown a distal portion of the push pin 290 is disposed within the needle 260, and a proximal portion of the push pin 290 is disposed within the needle housing 250. Further, as shown, at a proximal portion of the push pin 290 is disposed within the second cavity of the needle housing 250, an intermediate portion of the push pin 290 is disposed within the first cavity of the needle housing 250, and the push pin 290 passes through the thru-hole of the needle housing 250. As shown, a distal end of the needle 260 extends beyond the distal end of the needle housing 250. In some embodiments, a distal end of the needle 260 extends beyond the distal end of the needle housing 250 by about 1, 2, 3, 4, 5, 6, 7, 8, 9, or 10 mm or more. In some embodiments, a distal end of the needle 260 extends beyond the distal end of the needle housing 250 by at least about 1, 2, 3, 4, 5, 6, 7, 8, 9, or 10 mm. In some embodiments, a distal end of the needle 260 extends beyond the distal end of the needle housing 250 by at most about 1, 2, 3, 4, 5, 6, 7, 8, 9, or 10 mm.

As shown, the push rod of the push pin 290 translates within the needle lumen. Further as shown, the push rod has an outer diameter of less than the inner diameter of the needle 260. Alternatively, in some embodiments, the head has an outer diameter greater than the inner diameter of the needle 260. In some embodiments, the head does not fit within the needle 260. In some embodiments, at least a portion of the head does not fit within the needle 260. In some embodiments, the push pin 290 is dimensioned and positioned in the needle lumen such that distal translating of the push pin 290 pushes the implant positioned inside the needle lumen. In some embodiments, the push pin 290 is dimensioned and positioned in the needle lumen such that distal translating of the push pin 290 pushes the implant positioned inside the needle lumen to out of the needle lumen. In some embodiments, the push pin 290 is dimensioned and positioned in the needle lumen such that distal translating of the push pin 290 pushes the implant positioned inside the needle lumen to out of the needle lumen into the eye of the patient. In some embodiments, a distal surface of the push rod of the push pin 290 contacts the distal portion of the implant during the extended position, the retracted position, or both of the plunger assembly 200.

In some embodiments, the implant has a shape of elongated cylinder. In some embodiments, the implant comprises a plurality of particles. In some embodiments, the implant has a cross sectional shape of a circle, a triangle, a square, a rectangle, or any other polygon.

In some embodiments, the needle 260 has a length such that the distal end of the needle 260 is within the needle seal when the needle assembly 210 is in the sheathed state. In some embodiments, the needle 260 has a length of about 5 mm to about 70 mm. In some embodiments, the needle 260 has a length of about 5 mm to about 10 mm, about 5 mm to about 15 mm, about 5 mm to about 20 mm, about 5 mm to about 25 mm, about 5 mm to about 30 mm, about 5 mm to about 35 mm, about 5 mm to about 40 mm, about 5 mm to about 45 mm, about 5 mm to about 50 mm, about 5 mm to about 60 mm, about 5 mm to about 70 mm, about 10 mm to about 15 mm, about 10 mm to about 20 mm, about 10 mm to about 25 mm, about 10 mm to about 30 mm, about 10 mm to about 35 mm, about 10 mm to about 40 mm, about 10 mm to about 45 mm, about 10 mm to about 50 mm, about 10 mm to about 60 mm, about 10 mm to about 70 mm, about 15 mm to about 20 mm, about 15 mm to about 25 mm, about 15 mm to about 30 mm, about 15 mm to about 35 mm, about 15 mm to about 40 mm, about 15 mm to about 45 mm, about 15 mm to about 50 mm, about 15 mm to about 60 mm, about 15 mm to about 70 mm, about 20 mm to about 25 mm, about 20 mm to about 30 mm, about 20 mm to about 35 mm, about 20 mm to about 40 mm, about 20 mm to about 45 mm, about 20 mm to about 50 mm, about 20 mm to about 60 mm, about 20 mm to about 70 mm, about 25 mm to about 30 mm, about 25 mm to about 35 mm, about 25 mm to about 40 mm, about 25 mm to about 45 mm, about 25 mm to about 50 mm, about 25 mm to about 60 mm, about 25 mm to about 70 mm, about 30 mm to about 35 mm, about 30 mm to about 40 mm, about 30 mm to about 45 mm, about 30 mm to about 50 mm, about 30 mm to about 60 mm, about 30 mm to about 70 mm, about 35 mm to about 40 mm, about 35 mm to about 45 mm, about 35 mm to about 50 mm, about 35 mm to about 60 mm, about 35 mm to about 70 mm, about 40 mm to about 45 mm, about 40 mm to about 50 mm, about 40 mm to about 60 mm, about 40 mm to about 70 mm, about 45 mm to about 50 mm, about 45 mm to about 60 mm, about 45 mm to about 70 mm, about 50 mm to about 60 mm, about 50 mm to about 70 mm, or about 60 mm to about 70 mm. In some embodiments, the needle 260 has a length of about 5 mm, about 10 mm, about 15 mm, about 20 mm, about 25 mm, about 30 mm, about 35 mm, about 40 mm, about 45 mm, about 50 mm, about 60 mm, or about 70 mm. In some embodiments, the needle 260 has a length of at least about 5 mm, about 10 mm, about 15 mm, about 20 mm, about 25 mm, about 30 mm, about 35 mm, about 40 mm, about 45 mm, about 50 mm, or about 60 mm. In some embodiments, the needle 260 has a length of at most about 10 mm, about 15 mm, about 20 mm, about 25 mm, about 30 mm, about 35 mm, about 40 mm, about 45 mm, about 50 mm, about 60 mm, or about 70 mm. In some embodiments, the length of the needle 260 is a maximum length, a minimum length, a normal length, or an average length.

Figure 7:
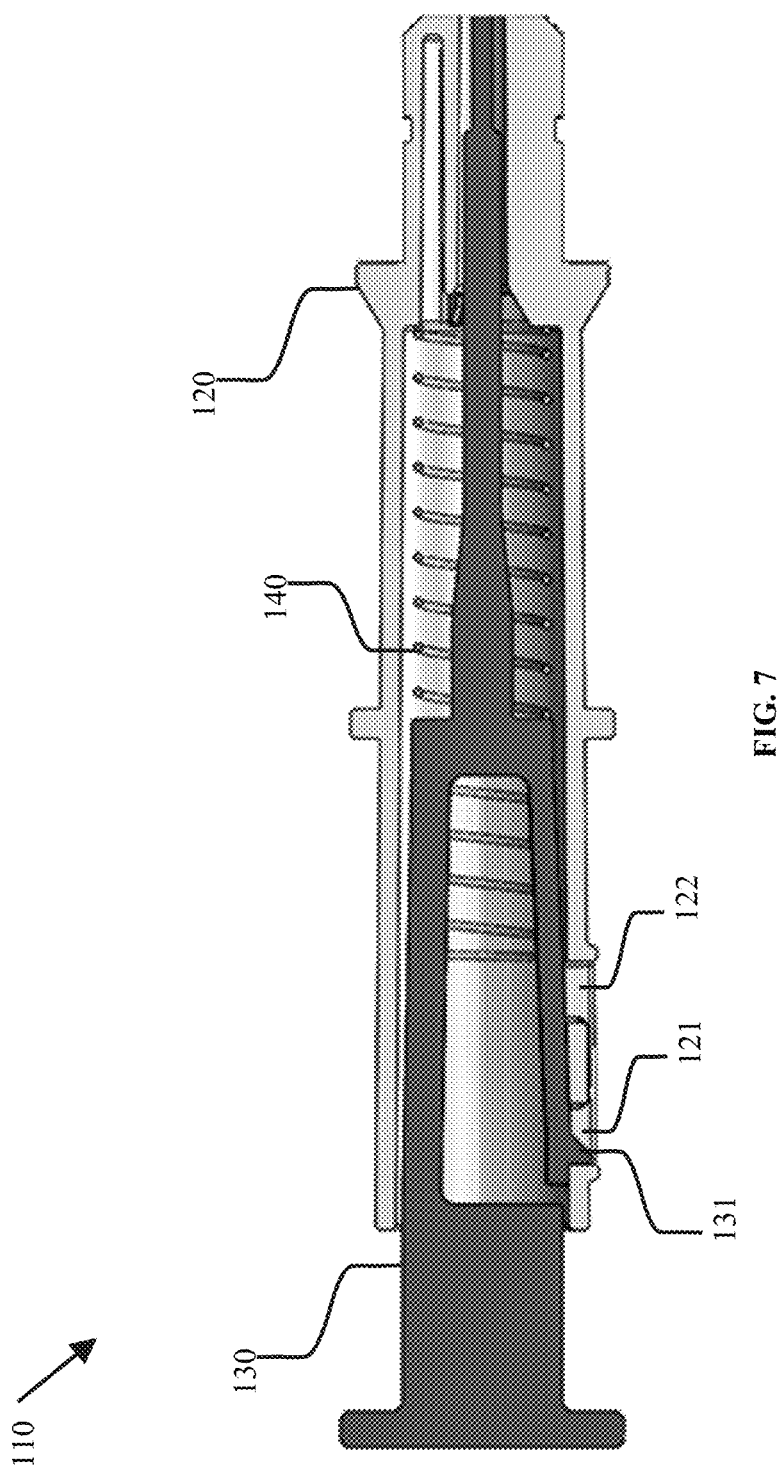
FIG. 7 shows a detailed cross-sectional illustration of a plunger assembly of the exemplary first injector system, per some embodiments herein.

As shown in FIGS. 4, 5, and 7 the injector system 100 comprises a plunger housing 120, a plunger 130, and a compression spring 140. As shown, the plunger 130 is slidably disposed within the plunger housing 120. Further, as shown, a distal end of the plunger 130 is adapted to engage and push the push pin 290 of the needle assembly 210 when in a distal position within the plunger housing 120.

In some embodiments, the distal end of the plunger 130 engages the head of the push pin 290 of the needle assembly 210. In some embodiments, the plunger 130 is manually actuated to translate distally within the plunger housing 120. In some embodiments, the plunger housing 120 is a syringe barrel. In some embodiments, the syringe barrel is a 1 mL syringe barrel. In some embodiments, a proximal end of the syringe plunger 130 protrudes beyond the plunger housing 120. In some embodiments, the plunger 130 is mechanically actuated to translate distally within the plunger housing 120. In some embodiments, the plunger assembly 110 further comprises a compression spring 140 biasing the plunger 130 towards a proximal end of the plunger housing 120. In some embodiments, the compression spring 140 has a distal end connected to the plunger housing 120 and a proximal end connected to the plunger 130. In some embodiments, per FIG. 19, the plunger housing 120 is a biopsy punch.

In some embodiments, the plunger 130 comprises a first stop feature 131, wherein the plunger housing 120 comprises a second stop 121 122 feature engageable with the first stop feature 131. In some embodiments, the second stop feature comprises a primary second stop 121 and a secondary second stop 122. In some embodiments, the first stop feature 131 engages with the primary second stop 121 in the retracted position of the plunger assembly 110. In some embodiments, the first stop feature 131 engages with the secondary second stop 122 in the extended position of the plunger assembly 110. In some embodiments, the first stop feature 131 engages with the secondary second stop 122 only in the unsheathed state of the needle assembly 210. In some embodiments, the first stop feature 131 engages with the secondary second stop 122 in the extended position of the plunger assembly 110, wherein upon implantation, distal force on the plunger advances the first stop feature 131 past the secondary second stop 122 by a retraction distance, whereafter reduction or release of the distal force returns the first stop feature 131 proximally by the retraction distance to engage with the secondary second stop 122. As shown, the first stop feature 131 comprises a flexure, wherein the primary second stop 121 and the secondary second stop 122 comprise a slot. Alternatively, the first stop feature 131 comprises a snap, a detent, a spring, a clip, or any combination thereof. Alternatively, at least one of the primary second stop 121 and the secondary second stop 122 comprise a snap, a detent, a spring, a clip, or any combination thereof. Further as shown, the secondary second stop 122 is distal to the primary second stop 121. In some embodiments, a distance between the primary second stop 121 and the secondary second stop 122 determines the distance that the plunger 130 translates from the extended position to the retracted position. In some embodiments, a distance between the primary second stop 121 and the secondary second stop 122 determines the distance that the push pin 290 translates. In some embodiments, a distance between the primary second stop 121 and the secondary second stop 122 determines the distance that the implant translates. In some embodiments, a distance between the primary second stop 121 and the secondary second stop 122 minus the length of the implant determines the distance that the implant is deposited into the eye of a subject.

As shown in FIGS. 4 and 5, the plunger 130 comprises a first plunger outer diameter and a second plunger outer diameter distal to the first plunger outer diameter, wherein the second plunger outer diameter is smaller than the first plunger outer diameter. In some embodiments, the first plunger outer diameter is larger than the inner diameter of the chamfered thru-hole in the push pin housing 230. In some embodiments, the second plunger outer diameter is smaller than the inner diameter of the chamfered thru-hole in the push pin housing 230.

Second Injector System

Figure 8:
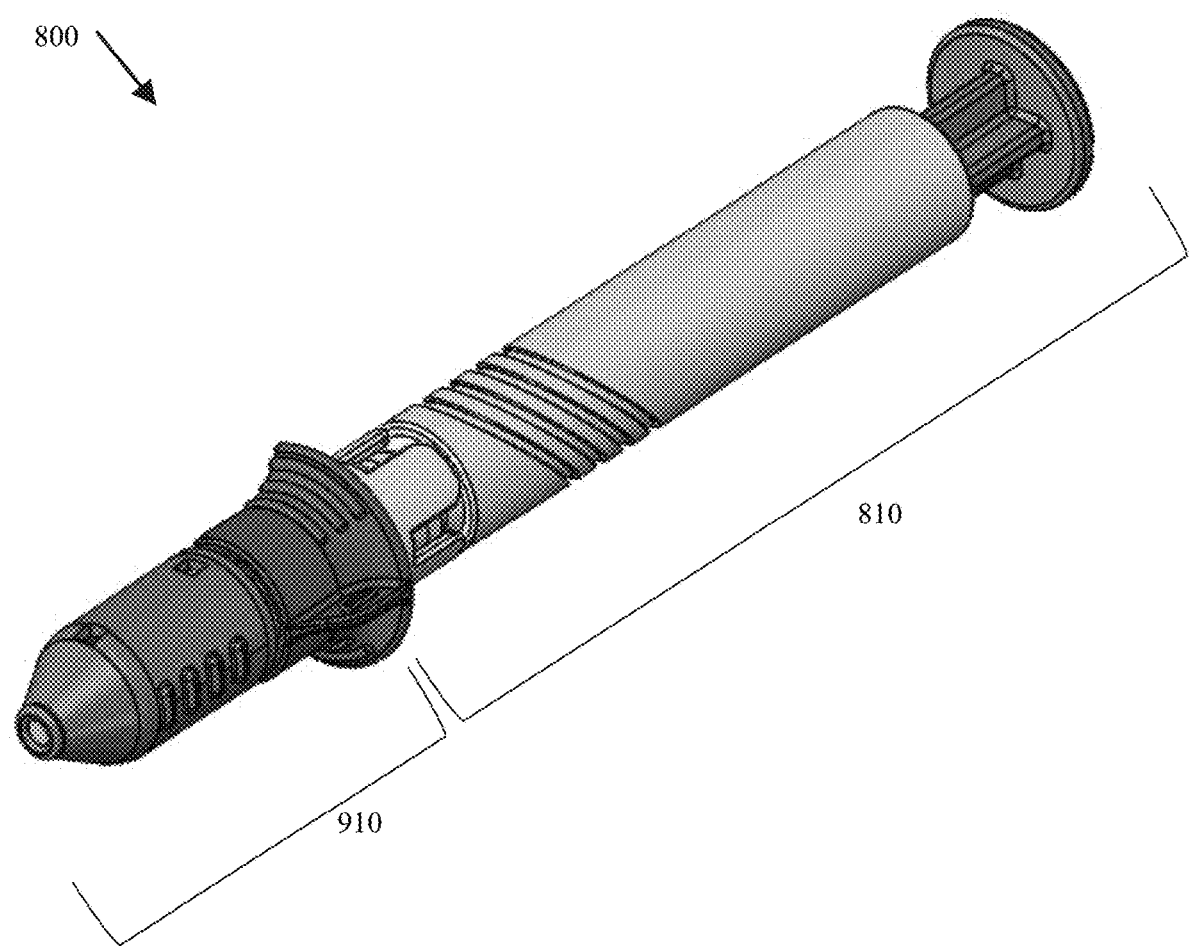
FIG. 8 shows a perspective illustration of an exemplary second injector system in a sheathed state, per some embodiments herein.
Figure 9:
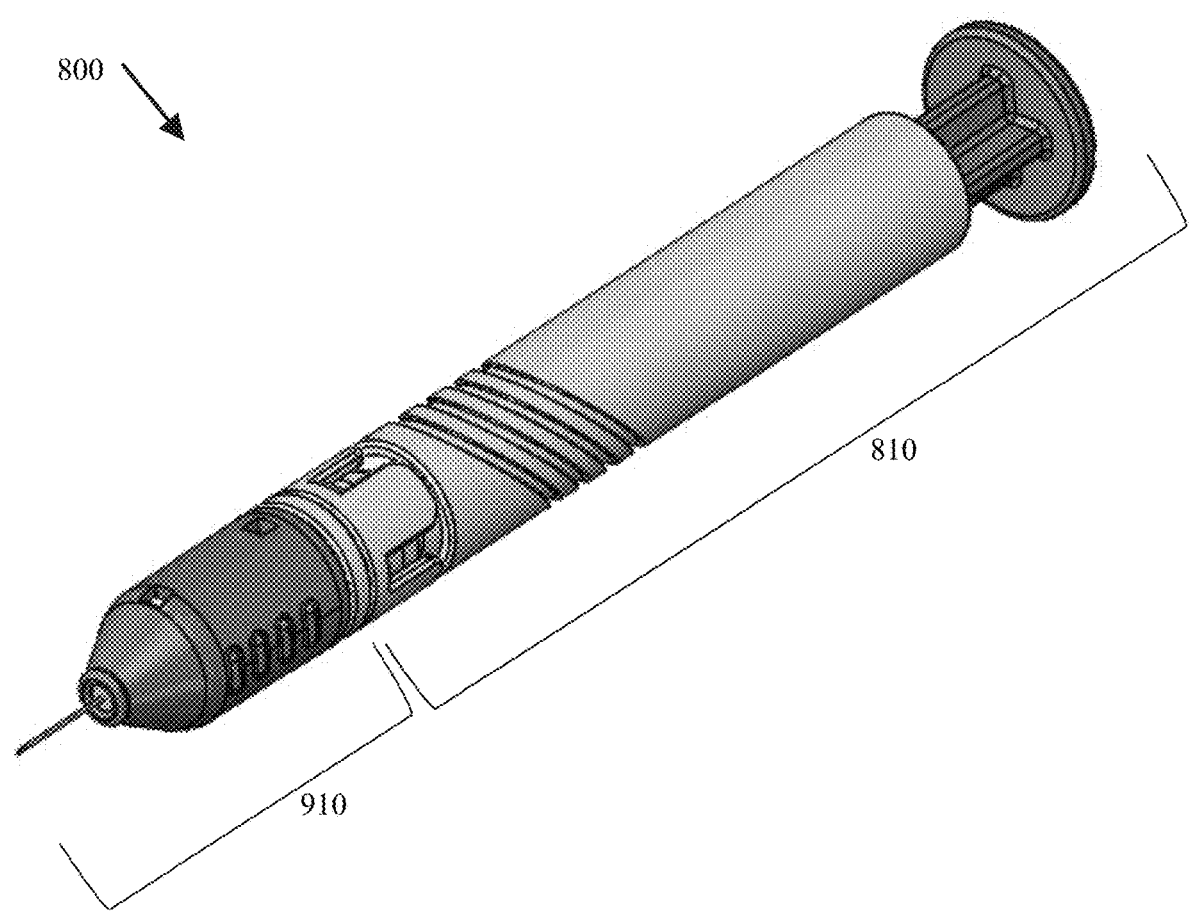
FIG. 9 shows a perspective illustration of an exemplary second injector system in an unsheathed state, per some embodiments herein.
Figure 10:
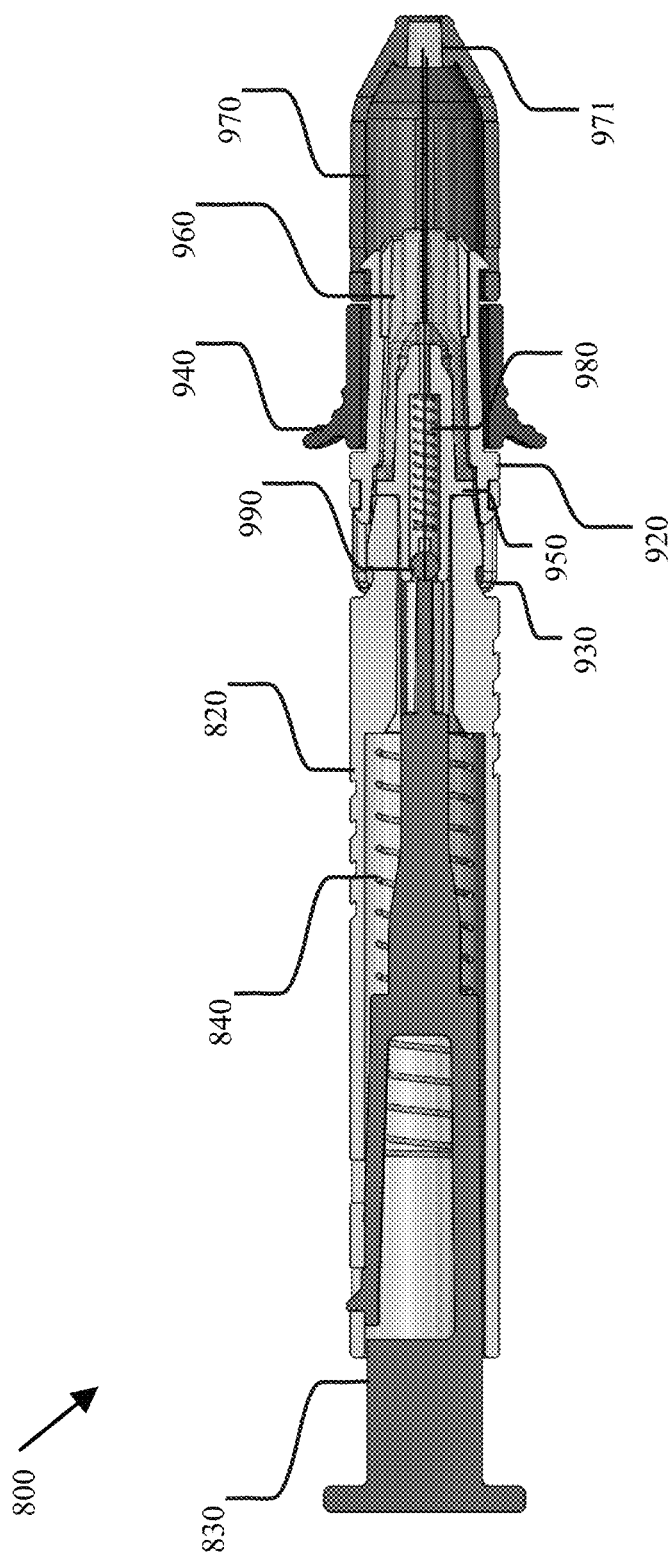
FIG. 10 shows a cross-sectional illustration of an exemplary second injector system in a sheathed state, per some embodiments herein.
Figure 11:
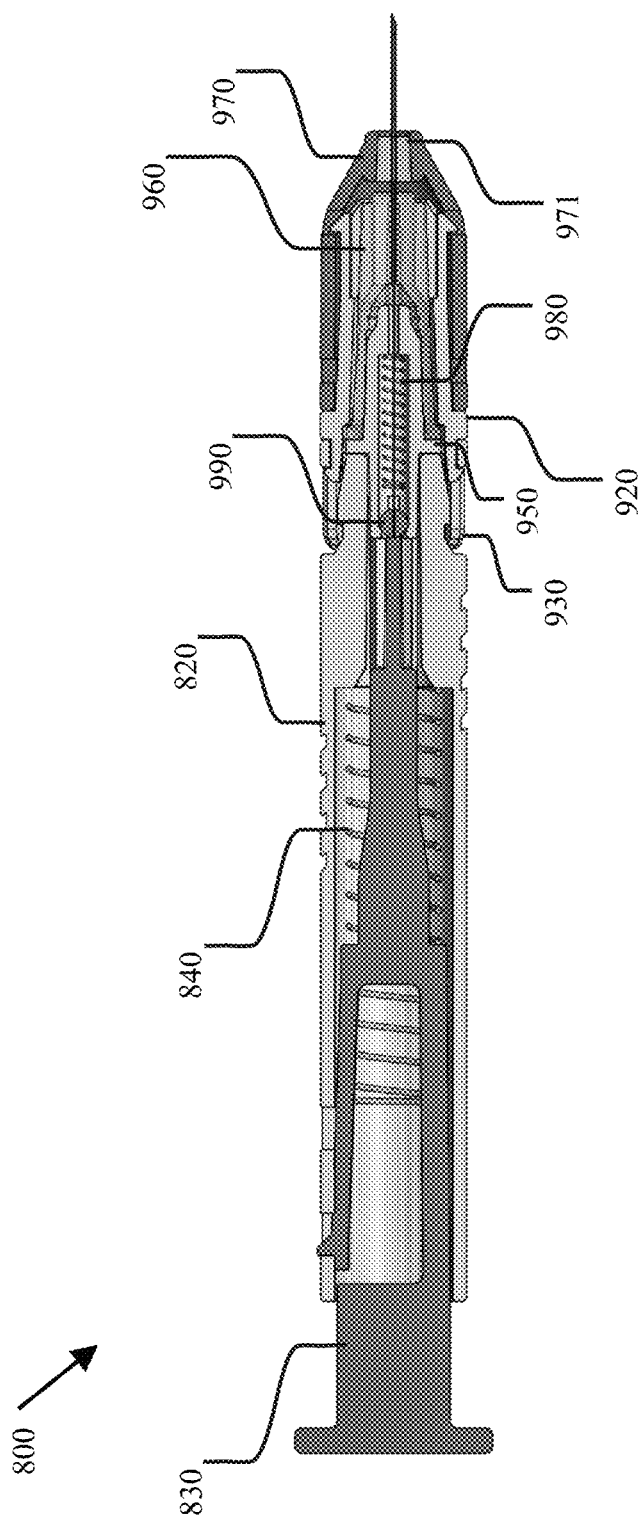
FIG. 11 shows a cross-sectional illustration of an exemplary second injector system in an unsheathed state, per some embodiments herein.
Figure 12:
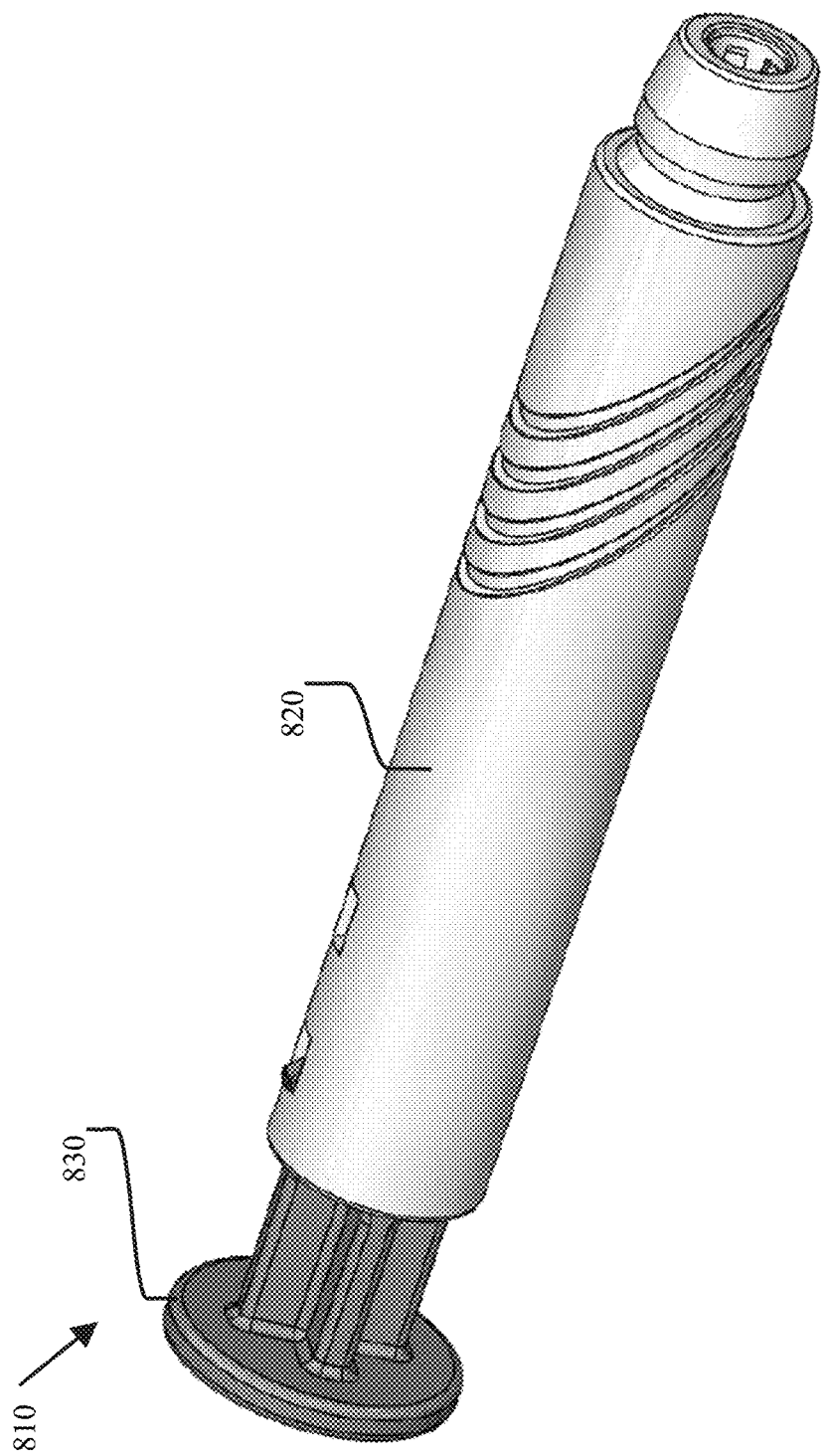
FIG. 12 shows a perspective illustration of a plunger assembly of an exemplary second injector system, per some embodiments herein.
Figure 13:
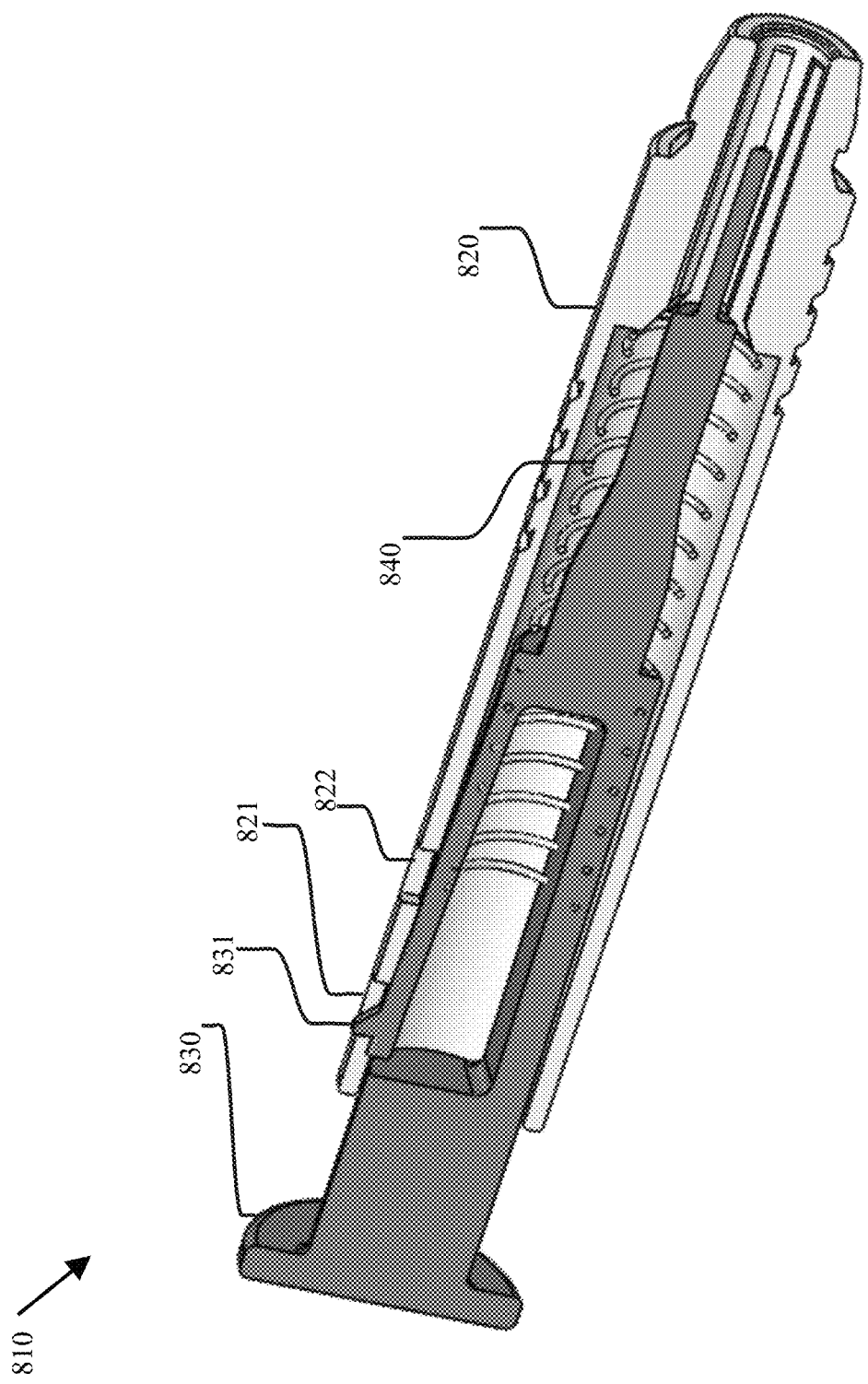
FIG. 13 shows a cross-sectioned perspective illustration of a plunger assembly of an exemplary second injector system, per some embodiments herein.
Figure 14:
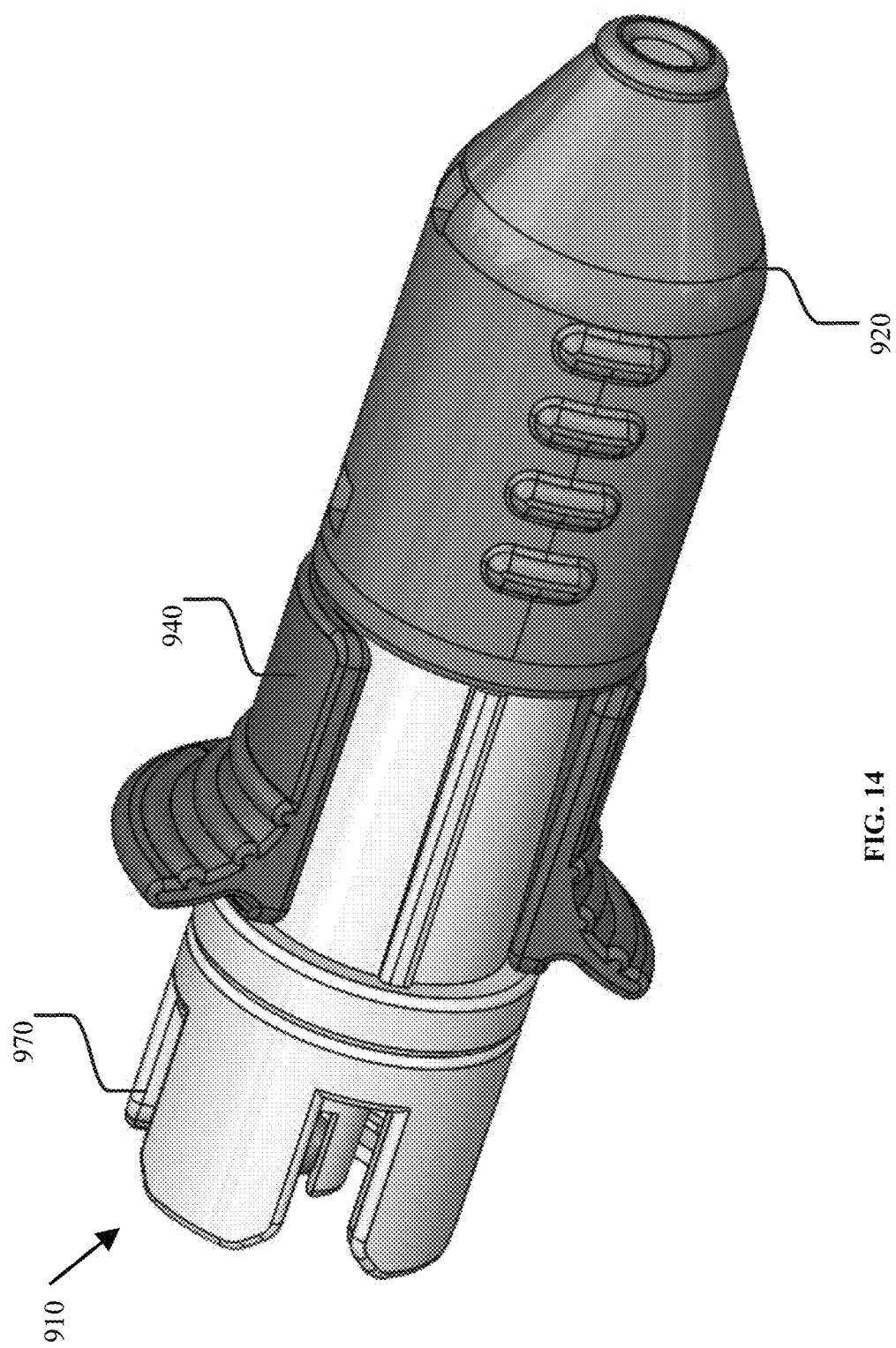
FIG. 14 shows a perspective illustration of a needle assembly of an exemplary second injector system, per some embodiments herein.
Figure 15:
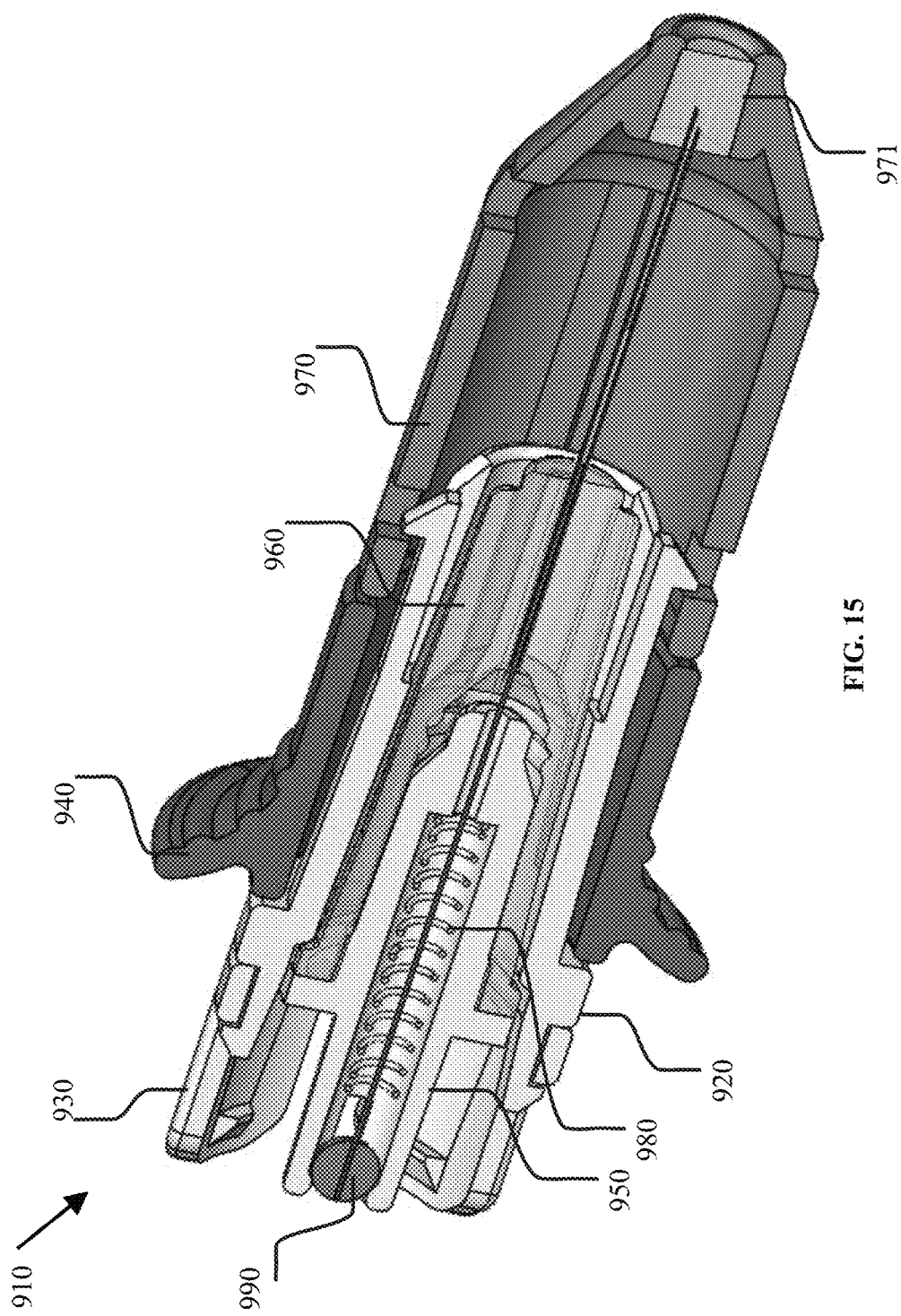
FIG. 15 shows a cross-sectioned perspective illustration of a needle assembly of an exemplary second injector system, per some embodiments herein.
Figure 16:
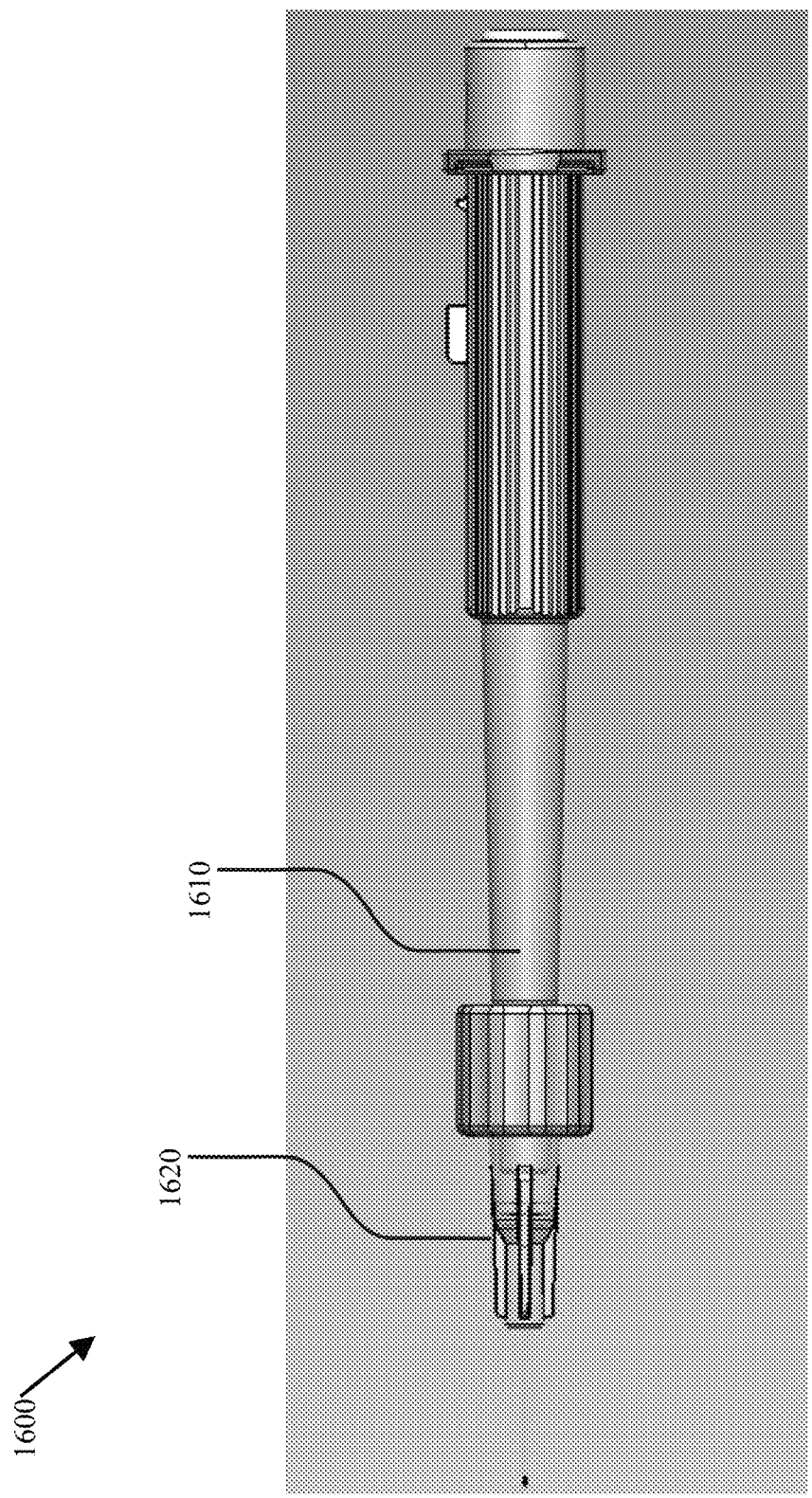
FIG. 16 shows a front view illustration of an exemplary injector system comprising a biopsy punch, per some embodiments herein.
Figure 17:
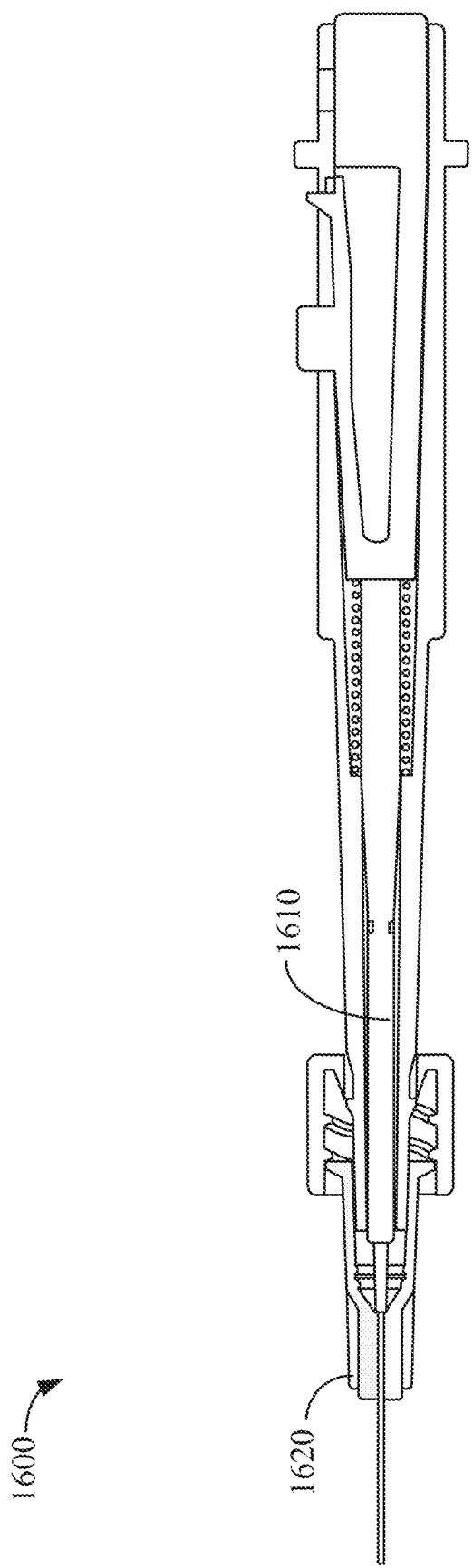
FIG. 17 shows a front cross-sectioned view illustration of the exemplary injector system comprising a biopsy punch, per some embodiments herein.

Provided herein per FIGS. 8-15 is a second injector system 800 for injecting an implant into an eye of a patient, the system comprising a needle assembly 910 and a plunger assembly 810. As shown, the needle assembly 910 removably couples to a distal end of the plunger assembly 810. In some embodiments, the needle assembly 910 removably couples to a distal end of the plunger assembly 810 by a snap, a screw, a pin, a band, a clamp, or any combination thereof. Alternatively, in some embodiments, the needle assembly 910 permanently couples to the plunger assembly 810. In some embodiments, the needle assembly 910 is maneuverable between a sheathed state and an unsheathed state. FIG. 8 shows a sheathed state of the needle assembly 910, and FIG. 2 shows an unsheathed state of the needle assembly 910. In some embodiments, the plunger assembly 810 is maneuverable between an extended position and a retracted position.

As seen per FIGS. 10, 11, 14, and 15 the exemplary needle assembly 910 comprises a needle housing 950, a needle 960, and a push pin 990. In some embodiments, the needle assembly 910 further comprises the implant loaded in the needle 960. In some embodiments, the needle assembly 910 further comprises the implant loaded in a lumen of the needle 960.

As shown, the needle housing 950 has a proximal end and a distal end. Further, as shown, the needle housing 950 comprises a male luer taper, a thru-hole, a first cavity, and a second cavity. Alternatively, in some embodiments, the needle housing 950 does not comprise one or more of the male luer taper, the thru-hole, the first cavity, and the second cavity. In some embodiments, two or more of the male luer taper, the thru-hole, the first cavity, and the second cavity are concentric. As shown, a distal termination of the first cavity is distal to the distal termination of the male luer taper. As shown, a proximal termination of the first cavity is distal to the distal termination of the male luer taper.

As shown, the needle 960 comprises a needle lumen at the distal end of the needle 960 and a female luer taper at the proximal end of the needle 960. In some embodiments, the needle 960 has a gauge of 90 to 40. In some embodiments, the needle 960 has a gauge of 90 to 92, 90 to 94, 90 to 96, 90 to 98, 90 to 30, 90 to 32, 90 to 34, 90 to 36, 90 to 38, 90 to 40, 92 to 94, 92 to 96, 92 to 98, 92 to 30, 92 to 32, 92 to 34, 92 to 36, 92 to 38, 92 to 40, 94 to 96, 94 to 98, 94 to 30, 94 to 32, 94 to 34, 94 to 36, 94 to 38, 94 to 40, 96 to 98, 96 to 30, 96 to 32, 96 to 34, 96 to 36, 96 to 38, 96 to 40, 98 to 30, 98 to 32, 98 to 34, 98 to 36, 98 to 38, 98 to 40, 30 to 32, 30 to 34, 30 to 36, 30 to 38, 30 to 40, 32 to 34, 32 to 36, 32 to 38, 32 to 40, 34 to 36, 34 to 38, 34 to 40, 36 to 38, 36 to 40, or 38 to 40. In some embodiments, the needle 960 has a gauge of 90, 92, 94, 96, 98, 30, 32, 34, 36, 38, or 40. In some embodiments, the needle 960 has a gauge of at least 90, 92, 94, 96, 98, 30, 32, 34, 36, or 38. In some embodiments, the needle 960 has a gauge of at most 92, 94, 96, 98, 30, 32, 34, 36, 38, or 40. In some embodiments, the needle 960 has a gauge of 93 to 30. In some embodiments, the needle 960 has a gauge of 93. In some embodiments, the needle 960 has a gauge of 30. In some embodiments, the needle 960 is straight. In some embodiments, the needle 960 is curved. In some embodiments, the curved needle 960 has a curvature radius of about 80, 90, 30, 40, 50, 60, 70, 80, 90 mm or more. In some embodiments, the needle 960 is twisted. In some embodiments, the twisted needle 960 has a pitch of about 5, 80, 85, 90, 95, 30, 35, 40, 45, 50 mm or more. In some embodiments, the twisted needle 960 has a maximum outer diameter of about 5, 80, 85, 90, 95, 30, 35, 40, 45, 50 mm or more. In some embodiments, the needle 960 is a commercially available needle.

As shown in FIGS. 10, 11, 14, and 15 the exemplary push pin 990 has a head and a push rod. Further, as shown, the head is positioned proximally to the push rod. As shown a proximal end of the needle 960 is coupled to the distal end of the needle housing 950 and the push pin 990 is disposed within the needle housing 950. Alternatively, in some embodiments, a proximal end of the needle 960 is within the needle housing 950. As shown, the push rod of the push pin 990 has an outer diameter of less than the inner diameter of the thru-hole of the needle housing 950.

As shown in FIGS. 10, 11, 14, and 15, the needle assembly 910 further comprises a resilient member 980 disposed within the needle housing 950. In some embodiments, the resilient member 980 proximally biases the push pin 990. In some embodiments, the resilient member 980 proximally biases the push pin 990 when the needle assembly 910 is in a sheathed state. In some embodiments, the resilient member 980 proximally biases the push pin 990 when the needle assembly 910 is in an unsheathed state. As shown, the resilient member 980 is a spring. Alternatively, in some embodiments, the resilient member 980 is a flexure, a piston, a motor, a band, or any combination thereof. In some embodiments, the resilient member 980 is disposed within and constrained by the first cavity of the needle housing 950. In some embodiments, the resilient member 980 has an outer diameter of less than an inner diameter of the first cavity of the needle housing 950. As shown, the push rod of the push pin 990 has an outer diameter of less than an inner diameter of the resilient member 980.

As shown in FIGS. 10, 11, 14, and 15, the needle assembly 910 further comprises a needle sheath 970 surrounding at least a portion of the needle housing 950, and having a distal portion surrounding the distal end of the needle 960. In some embodiments, a proximal portion of the needle sheath 970 surrounds the distal end of the needle housing 950. In some embodiments, a distal face of the needle sheath 970 is more distal to the needle housing 950 in the sheathed state of the needle assembly 910 than in the unsheathed state of the needle assembly 910. In some embodiments, a distal face of the needle sheath 970 is more distal to the plunger housing 120 in the sheathed state of the needle assembly 910 than in the unsheathed state of the needle assembly 910.

In some embodiments, when the needle assembly 910 is the sheathed, the needle 960 is entirely surrounded by the needle sheath 970. In some embodiments, when the needle assembly 910 is in the unsheathed state, at least a portion of the needle 960 extends distally beyond the needle sheath 970. In some embodiments, the distal portion of the needle sheath 970 abuts the eye of the patient when the implant is ejected from the needle lumen. In some embodiments, the distal portion of the needle sheath 970 abuts the eye of the patient when the needle assembly 910 is in its sheathed state. In some embodiments, the distal portion of the needle sheath 970 abuts the eye of the patient when the needle assembly 910 is in its unsheathed state. In some embodiments, the distal portion of the needle sheath 970 abuts the eye of the patient when the needle lumen is within the eye of the patient. In some embodiments, the distal portion of the needle sheath 970 abuts the eye of the patient when the needle lumen is within the needle sheath 970. In some embodiments, the needle sheath 970 is removable from the needle housing 950. In some embodiments, the needle sheath 970 is removable from the needle housing 950 by translation of the needle sheath 970 in a distal direction with respect to the needle housing 950. In some embodiments, the needle sheath 970 is removable from the needle housing 950 by translation of the needle sheath 970 in a proximal direction with respect to the needle housing 950.

As shown in FIGS. 10, 11, 14, and 15, the second injector system 800 further comprises a needle seal 971 at the distal end of the needle 960 that seals the distal end of the needle lumen. In some embodiments, the needle seal 971 is within a distal portion of the needle sheath 970. In some embodiments, the needle seal 971 is molded within a distal portion of the needle sheath 970. In some embodiments, the needle seal 971 is adhered or coupled to a distal portion of the needle sheath 970. In some embodiments, the needle seal 971 is formed of a polymer. In some embodiments, the polymer is rubber, plastic, or both. In some embodiments, the needle seal 971 is removable. In some embodiments, translating the needle sheath 970 in a proximal direction causes the needle 960 to pierce the needle seal 971.

As shown in FIGS. 10, 11, 14, and 15, the second injector system 800 further comprises a collar 940, a plunger attachment sleeve 930, and a collar sleeve 920. Further, as shown the collar sleeve 920 couples to at least one of the needle housing 950, the plunger attachment sleeve 930, or the needle sheath 970. As shown some embodiments, the collar sleeve 920 couples to the needle sheath 970 by a snap. Alternatively, in some embodiments, the collar sleeve 920 couples to the needle sheath 970 via a clip, a magnet, a screw, a bolt, a nut, an adhesive, or any combination thereof. Further, as shown the plunger attachment sleeve 930 couples to the needle housing, the collar sleeve 920, or both by a snap. Alternatively, the plunger attachment sleeve 930 couples to the needle housing, the collar sleeve 920, or both by a clip, a magnet, a screw, a bolt, a nut, an adhesive, or any combination thereof. As shown a distal outer diameter of the plunger attachment sleeve 930 is greater than an inner diameter of the second cavity of the needle housing 950. Also as shown, the plunger attachment sleeve 930 removably connects to the plunger housing 820.

As shown, the collar 940 couples to the collar sleeve 920. In some embodiments, the collar 940, when coupled to the collar sleeve 920, prevents the needle sheath 970 from translating in a distal direction, a proximal direction or both. In some embodiments, the collar 940, when decoupled from the collar sleeve 920, allows the needle sheath 970 to translate in a distal direction, a proximal direction or both. In some embodiments, the needle assembly 910 is in a sheathed state, per FIG. 10, when the collar 940 is coupled to the collar sleeve 920. In some embodiments, the needle assembly 910 is in an unsheathed state, per FIG. 11, when the collar 940 is decoupled from the collar sleeve 920. In some embodiments, the collar 940 couples to the collar sleeve 920 by rotating the collar 940, translating the collar 940, or both with respect to the collar sleeve 920. In some embodiments, the collar 940 decouples from the collar sleeve 920 by rotating the collar 940, translating the collar 940, or both with respect to the collar sleeve 920.

As shown in FIGS. 10, 11, 14, and 15, at least one of the push pin 990, the needle housing 950 and the needle 960 is dimensioned such that translating the push pin 990 in a distal direction ejects the implant positioned inside the needle lumen out of the needle lumen and into the eye of the patient. In some embodiments, at least one of the push pin 990, the needle housing 950 and the needle 960 is dimensioned such that translating the push pin 990 in a distal direction partially ejects the implant out of the needle lumen. In some embodiments, at least one of the push pin 990, the needle housing 950 and the needle 960 is dimensioned such that translating the push pin 990 in a distal direction completely ejects the implant out of the needle lumen. In some embodiments, at least one of the push pin 990, the needle housing 950 and the needle 960 is dimensioned such that translating the push pin 990 in a distal direction completely ejects the implant out of the needle lumen by 8, 9, 3, 4, 5, 6, 7, 8, 9, 80 mm or more.

In some embodiments, at least one of the push pin 990, the needle housing 950, and the needle 960 is dimensioned such that translating the push pin 990 in a distal direction positions a distal end of the push rod of the push pin 990 distal to the distal end of the needle 960. In some embodiments, at least one of the push pin 990, the needle housing 950, and the needle 960 is dimensioned such that translating the push pin 990 in a distal direction positions a distal end of the push rod of the push pin 990 distal to the distal end of the needle 960 by 8, 9, 3, 4, 5, 6, 7, 8, 9, 80 mm or more. In some embodiments, at least one of the push pin 990, the needle housing 950 and the needle 960 is dimensioned such that translating the push pin 990 in a distal direction positions a distal end of the push rod of the push pin 990 proximal to the distal end of the needle 960. In some embodiments, at least one of the push pin 990, the needle housing 950 and the needle 960 is dimensioned such that translating the push pin 990 in a distal direction positions a distal end of the push rod of the push pin 990 proximal to the distal end of the needle 960 by 8, 9, 3, 4, 5, 6, 7, 8, 9, 80 mm or more.

In some embodiments, the needle 960 has a length such that the distal end of the needle 960 is within the needle seal when the needle assembly 910 is in a sheathed state. Further, as shown, at least a portion of the push rod of the push pin 990 is disposed within the needle 960, and at least a portion of the push pin 990 is disposed within the needle housing 950. As shown a distal portion of the push pin 990 is disposed within the needle 960, and a proximal portion of the push pin 990 is disposed within the needle housing 950. Further, as shown, a proximal portion of the push pin 990 is disposed within the second cavity of the needle housing 950, an intermediate portion of the push pin 990 is disposed within the first cavity of the needle housing 950, and the push pin 990 passes through the thru-hole of the needle housing 950. As shown, a distal end of the needle 960 extends beyond the distal end of the needle housing 950. In some embodiments, a distal end of the needle 960 extends beyond the distal end of the needle housing 950 by 8, 9, 3, 4, 5, 6, 7, 8, 9, 80 mm or more.

As shown, the push rod of the push pin 990 translates within the needle lumen. Further as shown, the push rod has an outer diameter of less than the inner diameter of the needle 960. Alternatively, in some embodiments, the head has an outer diameter greater than the inner diameter of the needle 960. In some embodiments, the head does not fit within the needle 960. In some embodiments, the push pin 990 is dimensioned and positioned in the needle lumen such that distal translating of the push pin 990 pushes the implant positioned inside the needle lumen. In some embodiments, the push pin 990 is dimensioned and positioned in the needle lumen such that distal translating of the push pin 990 pushes the implant positioned inside the needle lumen to out of the needle lumen. In some embodiments, the push pin 990 is dimensioned and positioned in the needle lumen such that distal translating of the push pin 990 pushes the implant positioned inside the needle lumen to out of the needle lumen into the eye of the patient. In some embodiments, a distal surface of the push rod of the push pin 990 contacts the distal portion of the implant during the sheathed state, the unsheathed state, or both of the needle assembly 910. In some embodiments, a distal surface of the push rod of the push pin 990 contacts the distal portion of the implant during a sheathed state of the device, an unsheathed state of the device, or both of the needle assembly 910.

In some embodiments, the implant has a shape of elongated cylinder. In some embodiments, the implant comprises a plurality of particles. In some embodiments, the implant has a cross sectional shape of a circle, a triangle, a square, a rectangle, or any other polygon.

In some embodiments, the needle 960 has a length such that the distal end of the needle 960 is within the needle seal when the needle assembly 910 is in a sheathed state. In some embodiments, the needle 960 has a length of about 5 mm to about 70 mm. In some embodiments, the needle 960 has a length of about 5 mm to about 80 mm, about 5 mm to about 85 mm, about 5 mm to about 90 mm, about 5 mm to about 95 mm, about 5 mm to about 30 mm, about 5 mm to about 35 mm, about 5 mm to about 40 mm, about 5 mm to about 45 mm, about 5 mm to about 50 mm, about 5 mm to about 60 mm, about 5 mm to about 70 mm, about 80 mm to about 85 mm, about 80 mm to about 90 mm, about 80 mm to about 95 mm, about 80 mm to about 30 mm, about 80 mm to about 35 mm, about 80 mm to about 40 mm, about 80 mm to about 45 mm, about 80 mm to about 50 mm, about 80 mm to about 60 mm, about 80 mm to about 70 mm, about 85 mm to about 90 mm, about 85 mm to about 95 mm, about 85 mm to about 30 mm, about 85 mm to about 35 mm, about 85 mm to about 40 mm, about 85 mm to about 45 mm, about 85 mm to about 50 mm, about 85 mm to about 60 mm, about 85 mm to about 70 mm, about 90 mm to about 95 mm, about 90 mm to about 30 mm, about 90 mm to about 35 mm, about 90 mm to about 40 mm, about 90 mm to about 45 mm, about 90 mm to about 50 mm, about 90 mm to about 60 mm, about 90 mm to about 70 mm, about 95 mm to about 30 mm, about 95 mm to about 35 mm, about 95 mm to about 40 mm, about 95 mm to about 45 mm, about 95 mm to about 50 mm, about 95 mm to about 60 mm, about 95 mm to about 70 mm, about 30 mm to about 35 mm, about 30 mm to about 40 mm, about 30 mm to about 45 mm, about 30 mm to about 50 mm, about 30 mm to about 60 mm, about 30 mm to about 70 mm, about 35 mm to about 40 mm, about 35 mm to about 45 mm, about 35 mm to about 50 mm, about 35 mm to about 60 mm, about 35 mm to about 70 mm, about 40 mm to about 45 mm, about 40 mm to about 50 mm, about 40 mm to about 60 mm, about 40 mm to about 70 mm, about 45 mm to about 50 mm, about 45 mm to about 60 mm, about 45 mm to about 70 mm, about 50 mm to about 60 mm, about 50 mm to about 70 mm, or about 60 mm to about 70 mm. In some embodiments, the needle 960 has a length of about 5 mm, about 80 mm, about 85 mm, about 90 mm, about 95 mm, about 30 mm, about 35 mm, about 40 mm, about 45 mm, about 50 mm, about 60 mm, or about 70 mm. In some embodiments, the needle 960 has a length of at least about 5 mm, about 80 mm, about 85 mm, about 90 mm, about 95 mm, about 30 mm, about 35 mm, about 40 mm, about 45 mm, about 50 mm, or about 60 mm. In some embodiments, the needle 960 has a length of at most about 80 mm, about 85 mm, about 90 mm, about 95 mm, about 30 mm, about 35 mm, about 40 mm, about 45 mm, about 50 mm, about 60 mm, or about 70 mm. In some embodiments, the length of the needle 960 is a maximum length, a minimum length, a normal length, or an average length.

As shown in FIGS. 10-13 the second injector system 800 comprises a plunger housing 820, a plunger 830, and a compression spring 840. As shown, the plunger 830 is slidably disposed within the plunger housing 820. Further, as shown, a distal end of the plunger 830 is adapted to engage and push the push pin 990 of the needle assembly 910 when in a distal position within the plunger housing 820.

In some embodiments, the distal end of the plunger 830 engages the head of the push pin 990 of the needle assembly 910. In some embodiments, the plunger 830 is manually actuated to translate distally within the plunger housing 820. In some embodiments, the plunger housing 820 is a syringe barrel. In some embodiments, the syringe barrel is a 1 mL syringe barrel. In some embodiments, a proximal end of the syringe plunger 830 protrudes beyond the plunger housing 820. In some embodiments, the plunger 830 is mechanically actuated to translate distally within the plunger housing 820. In some embodiments, the plunger assembly 810 further comprises a compression spring 840 biasing the plunger 830 towards a proximal end of the plunger housing 820. In some embodiments, the compression spring 840 has a distal end connected to the plunger housing 820 and a proximal end connected to the plunger 830.

In some embodiments, the plunger 830 comprises a first stop feature 831, wherein the plunger housing 820 comprises a second stop 821 822 feature engageable with the first stop feature 831. In some embodiments, the second stop feature comprises a primary second stop 821 and a secondary second stop 822. In some embodiments, the primary second stop 821 engages with the first stop feature 831 in the sheathed state of the needle assembly 910. In some embodiments, the secondary second stop 822 engages with the first stop feature 831 in the unsheathed state of the needle assembly 910. In some embodiments, the primary second stop 821 engages with the first stop feature 831 in the sheathed state of the needle assembly 910, wherein upon implantation, distal force on the plunger advances the first stop feature 831 past the secondary second stop 822 by a retraction distance, whereafter reduction or release of the distal force returns the first stop feature 831 proximally by the retraction distance to engage with the secondary second stop 822. As shown, the first stop feature 831 comprises a flexure, wherein the primary second stop 821 and the secondary second stop 822 comprise a slot. Alternatively, the first stop feature 831 comprises a snap, a detent, a spring, a clip, or any combination thereof. Alternatively, at least one of the primary second stop 821 and the secondary second stop 822 comprise a snap, a detent, a spring, a clip, or any combination thereof. Further as shown, the secondary second stop 822 is distal to the primary second stop 821. In some embodiments, a distance between the primary second stop 821 and the secondary second stop 822 determines the distance that the plunger translates from the sheathed state to the unsheathed state of the needle assembly 910. In some embodiments, a distance between the primary second stop 821 and the secondary second stop 822 determines the distance that the push pin 990 translates. In some embodiments, a distance between the primary second stop 821 and the secondary second stop 822 determines the distance that the implant translates. In some embodiments, a distance between the primary second stop 821 and the secondary second stop 822 minus the length of the implant determines the distance that the implant is deposited into the eye of a subject.

Additional Injector Systems

Figure 18:
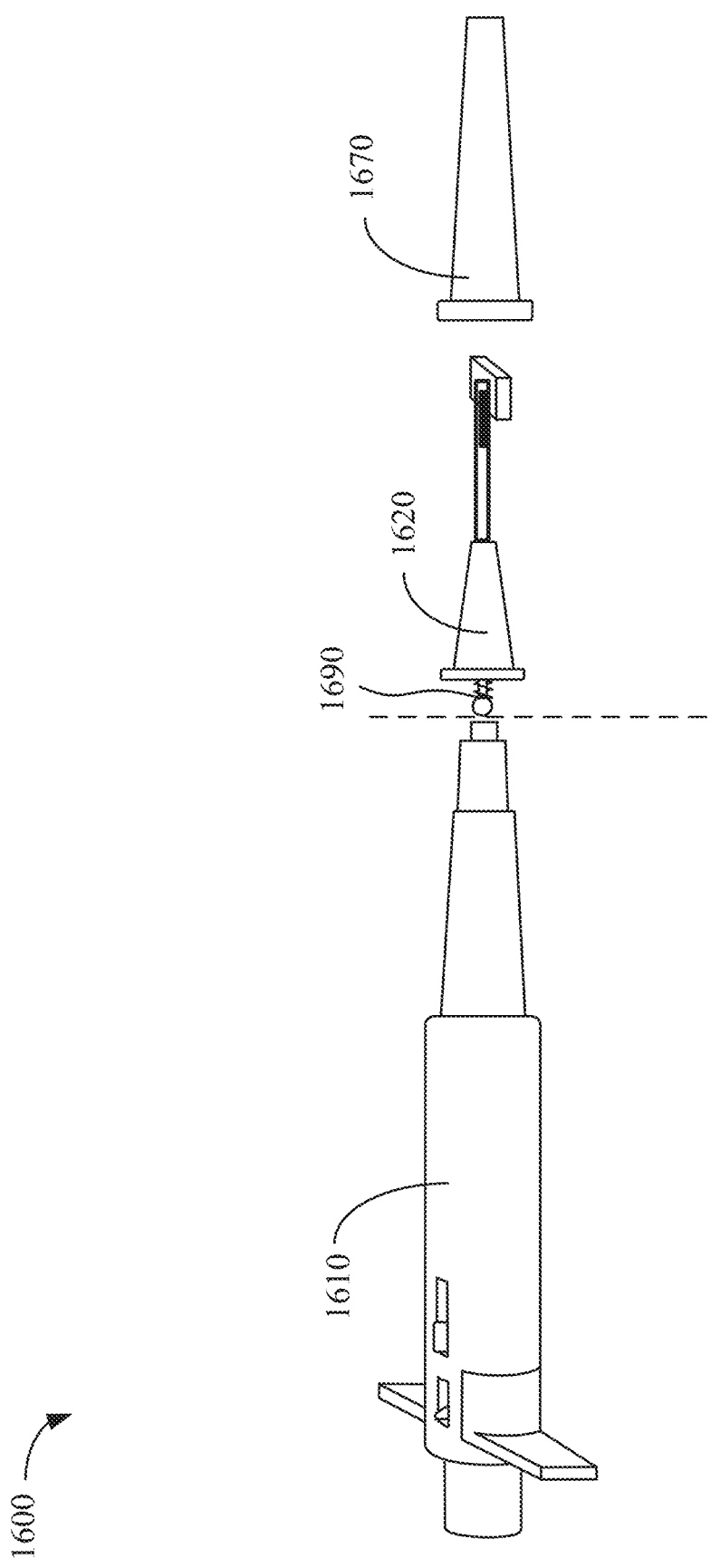
FIG. 18 shows an exploded illustration of the exemplary injector system comprising a biopsy punch, per some embodiments herein.

FIGS. 16-19 show illustrations of an exemplary injector system 1600 comprising a biopsy punch 1610. In some embodiments, the biopsy punch 1610 comprises a modified biopsy punch formed from a commercially available biopsy punch. In some embodiments, the biopsy punch injector system 1600 comprises a commercially available needle 1620 and a sheath 1670 surrounding at least a portion of the needle 1620. As shown in FIG. 18, the biopsy punch injector system 1600 comprises a push pin 1690 coupled to a distal surface of the biopsy punch 1610. In some embodiments, an implantable medicament is contained within the needle 1620. In some embodiments, distal translation of the biopsy punch 1610 translates the push pin 1690 to eject an implantable medicament out of the needle 1620.

In some embodiments, the needle 1620 has a gauge of 20 to 40. In some embodiments, the needle 1620 has a gauge of 20 to 22, 20 to 24, 20 to 26, 20 to 28, 20 to 30, 20 to 32, 20 to 34, 20 to 36, 20 to 38, 20 to 40, 22 to 24, 22 to 26, 22 to 28, 22 to 30, 22 to 32, 22 to 34, 22 to 36, 22 to 38, 22 to 40, 24 to 26, 24 to 28, 24 to 30, 24 to 32, 24 to 34, 24 to 36, 24 to 38, 24 to 40, 26 to 28, 26 to 30, 26 to 32, 26 to 34, 26 to 36, 26 to 38, 26 to 40, 28 to 30, 28 to 32, 28 to 34, 28 to 36, 28 to 38, 28 to 40, 30 to 32, 30 to 34, 30 to 36, 30 to 38, 30 to 40, 32 to 34, 32 to 36, 32 to 38, 32 to 40, 34 to 36, 34 to 38, 34 to 40, 36 to 38, 36 to 40, or 38 to 40. In some embodiments, the needle 1620 has a gauge of 20, 22, 24, 26, 28, 30, 32, 34, 36, 38, or 40. In some embodiments, the needle 1620 has a gauge of at least 20, 22, 24, 26, 28, 30, 32, 34, 36, or 38. In some embodiments, the needle 1620 has a gauge of at most 22, 24, 26, 28, 30, 32, 34, 36, 38, or 40. In some embodiments, the needle 1620 has a gauge of 23 to 30. In some embodiments, the needle 1620 has a gauge of 23. In some embodiments, the needle 1620 has a gauge of 30. In some embodiments, the needle 1620 is straight. In some embodiments, the needle 1620 is curved. In some embodiments, the curved needle 1620 has a curvature radius of about 10, 20, 30, 40, 50, 60, 70, 80, 90 mm or more. In some embodiments, the needle 1620 is twisted. In some embodiments, the twisted needle 1620 has a pitch of about 5, 10, 15, 20, 25, 30, 35, 40, 45, 50 mm or more. In some embodiments, the twisted needle 1620 has a maximum outer diameter of about 5, 10, 15, 20, 25, 30, 35, 40, 45, 50 mm or more.

Figure 19:
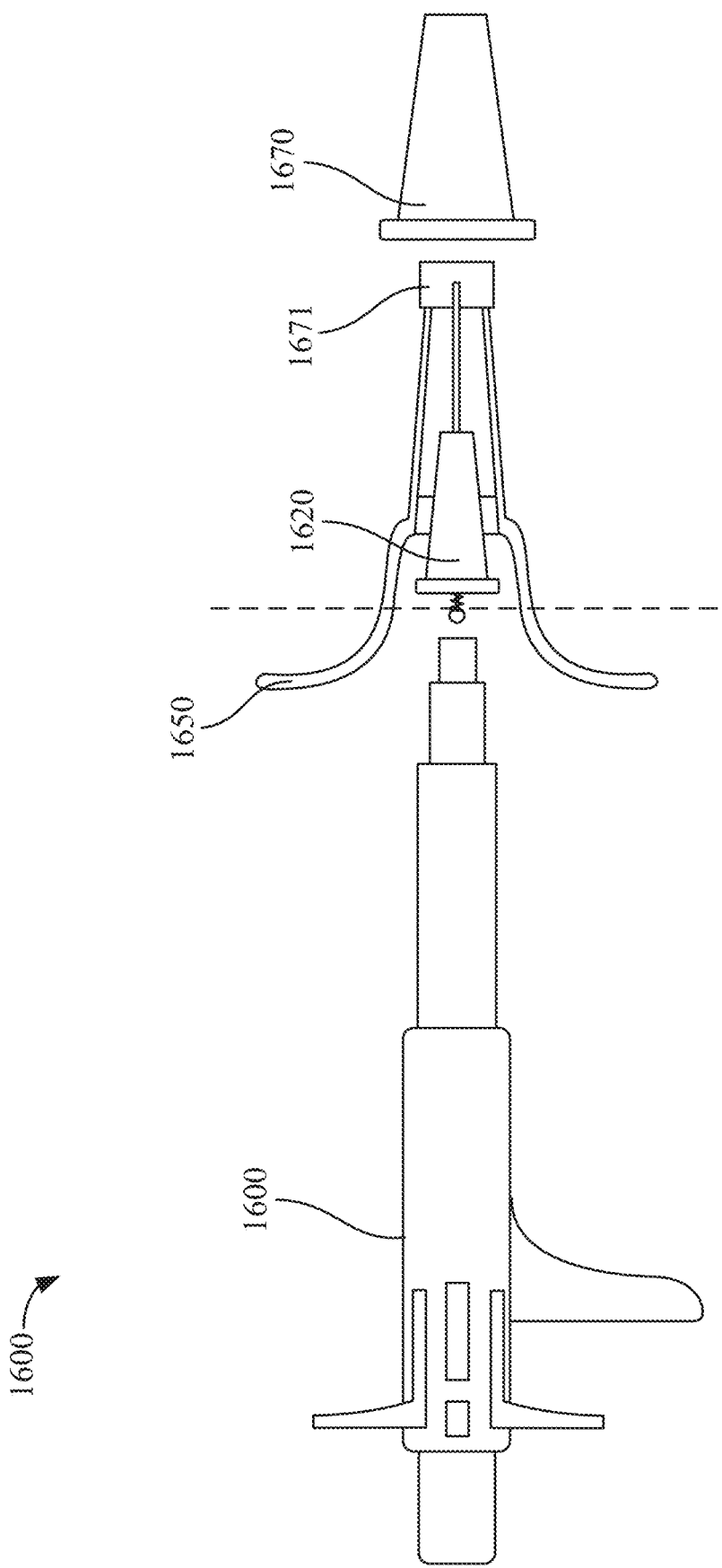
FIG. 19 shows an exploded illustration of an exemplary injector system comprising a biopsy punch and a retractable needle seal, per some embodiments herein.
Figure 20:
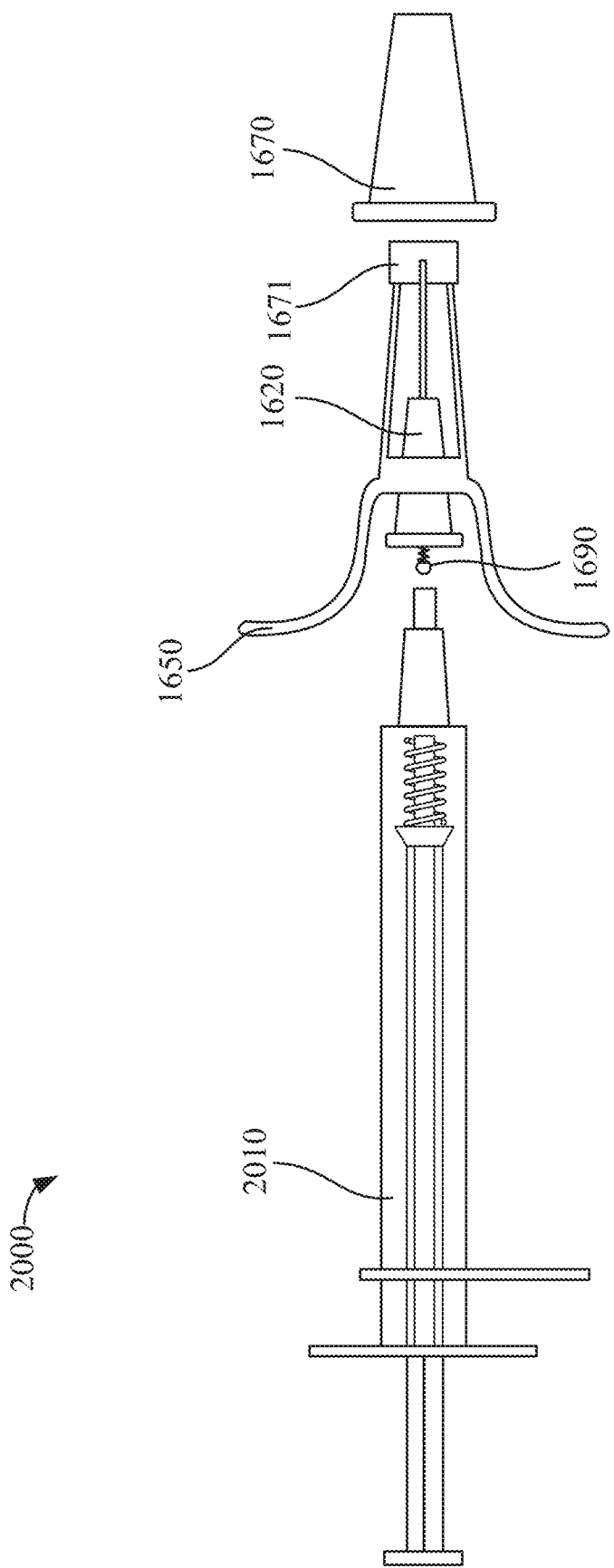
FIG. 20 shows exploded and cross-sectioned illustrations of an exemplary injector system comprising a syringe and a retractable needle seal, per some embodiments herein.

FIG. 19 shows an exemplary injector system 1600 comprising a biopsy punch 1610 and a retractable needle seal housing 1650. As shown, the retractable needle seal housing 1650 is slidably coupled to the needle 1620. Further as shown, the retractable needle seal housing 1650 translates with respect to the needle 1620 between a sheathed state and an unsheathed state. Further, as shown the retractable needle seal housing 1650 comprises a flange for manipulation of the system 1600, and a needle seal 1671. In some embodiments, the retractable needle seal housing 1650 comprises a needle seal 1671 that surrounds the distal end of the needle 1620 when the system 1600 is in the sheathed state. In some embodiments, the distal end of the needle 1620 is distal to the distal face of the distal plug of the needle seal 1671 when the system 1600 is in an unsheathed state. Additionally, as shown, the sheath 1670 removably attaches to the retractable needle seal housing 1650. In some embodiments, the needle seal 1671 of the retractable needle seal housing 1671 is made of silicone, plastic, or any other medical grade material.

Figure 21:
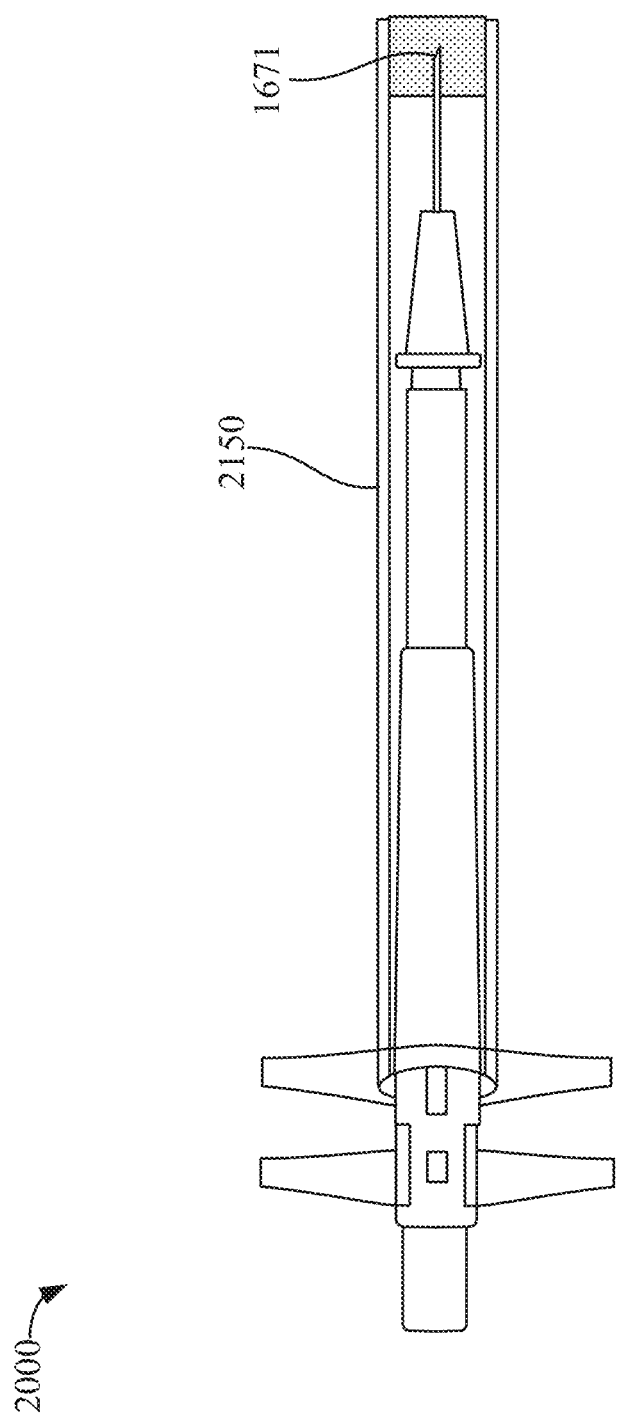
FIG. 21 shows an illustration of an exemplary injector system comprising a biopsy punch within a syringe or other full-length tube, per some embodiments herein.

FIGS. 20-24 show exemplary injector systems comprising a syringe 2010. Per FIG. 20, the injector system 2000 comprises the syringe 2010, a needle 1620, a sheath 1670 surrounding at least a portion of the needle 1620, and a retractable needle seal 1670 slidably coupled to the needle 1620. In some embodiments, the syringe 2010 comprises a 1 ml syringe. In some embodiments, the syringe 2010 comprises a commercially available syringe. As shown injector system 2000 comprises a push pin 1690 coupled to a distal surface of the syringe 2010. In some embodiments, an implantable medicament is contained within the needle 1620. In some embodiments, distal translation of the syringe 2010 translates the push pin 1690 to eject an implantable medicament out of the needle 1620. As seen in FIG. 21, in some embodiments, the sheath 1670 and the retractable needle seal 1671 of the injector system 2000 are a single retainer sheath component 2150, which extends proximally beyond the needle 1620. In some embodiments, the retainer sheath component 2150 provides an airtight seal against the syringe 2010.

Figure 22:
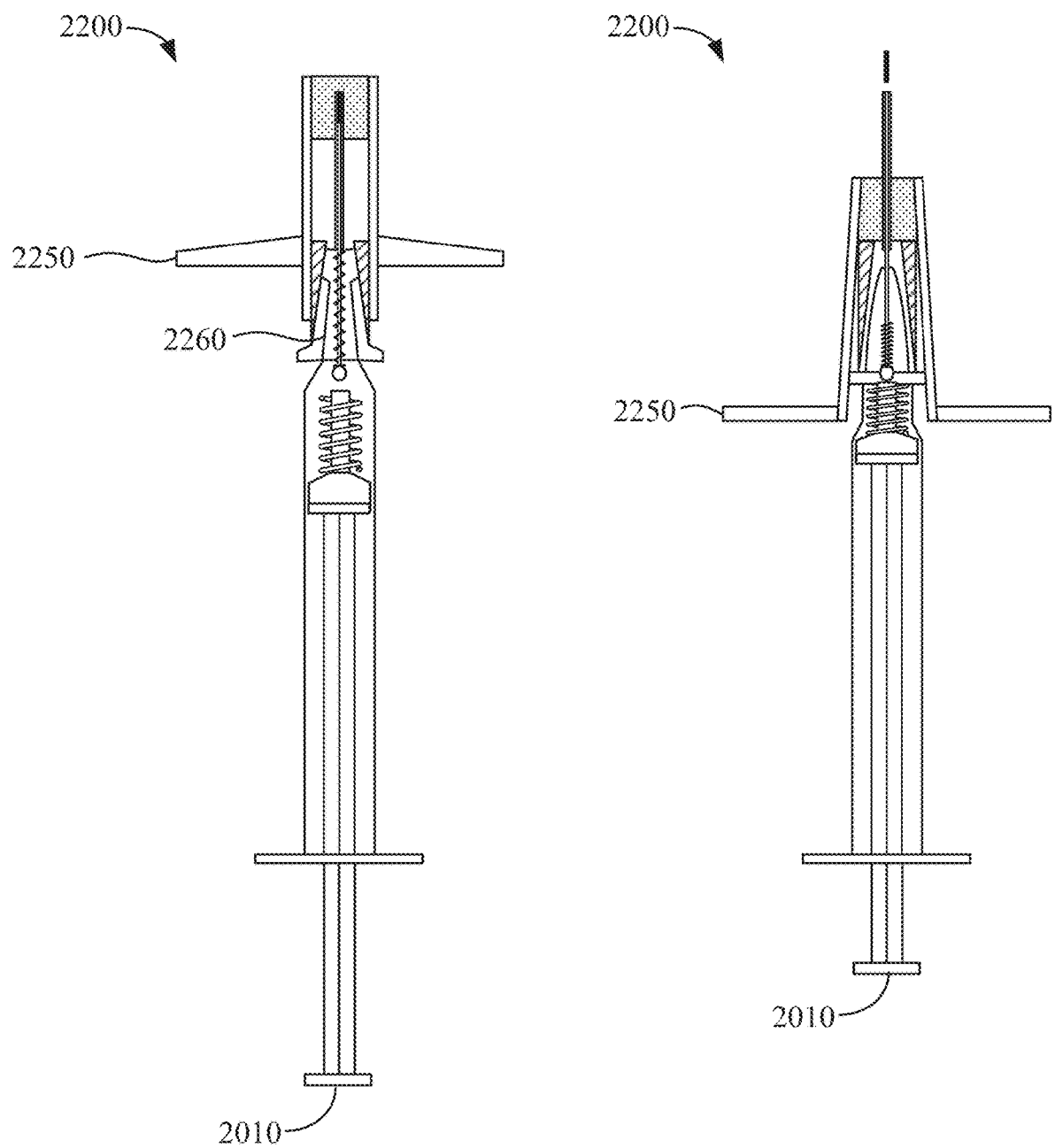
FIG. 22 shows illustrations of an exemplary injector system comprising a syringe and a primary needle and removable needle seal assembly in an unsheathed and a sheathed state, per some embodiments herein.

FIG. 22 shows illustrations of an exemplary injector system 2200 comprising a needle 2260 and removable needle seal assembly 2250 in a sheathed state (left) and an unsheathed state (right). As shown therein, the shape of the outer surface of the hub of the needle 2260 serves as a rail. In some embodiments, the rail has longitudinal bearing surfaces parallel to the retraction direction of the removable needle seal assembly. In some embodiments, the longitudinal bearing surface is either formed of ridges or has a cylindrical cross-sectional shape. In some embodiments, the longitudinal bearing surface enables retraction of the needle seal assembly. In some embodiments, the longitudinal bearing surface constrains against extension and retraction in directions other than parallel to the longitudinal needle lumen axis. In some embodiments, the longitudinal bearing surface enables linear retraction of the removable needle seal assembly to reduce bending loads on the needle 2260.

Figure 23:
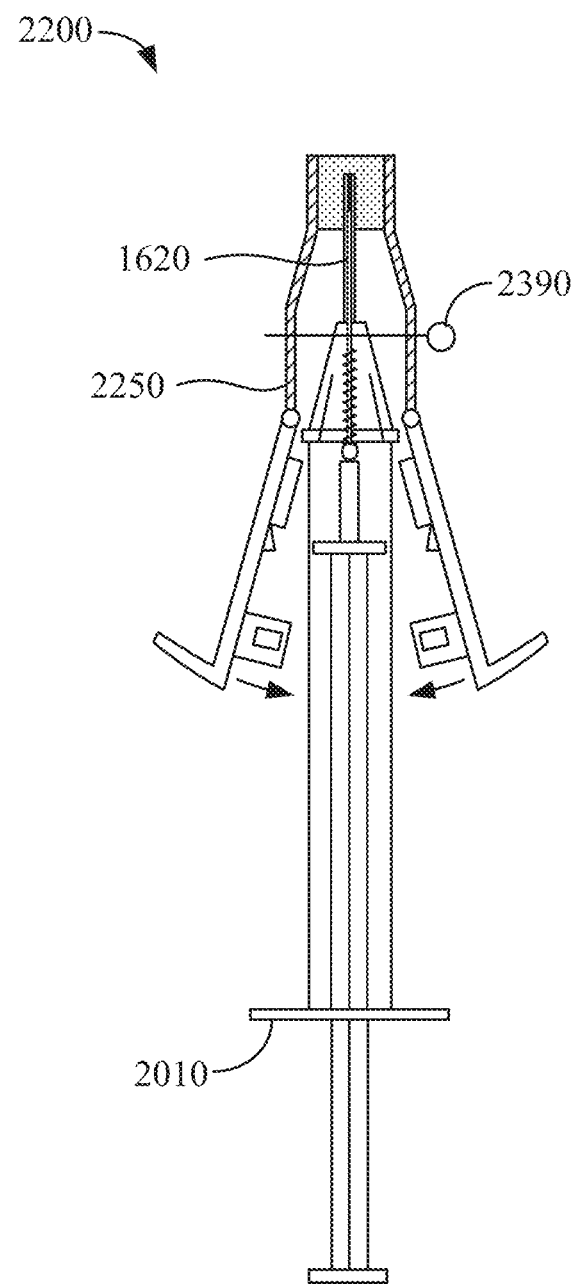
FIG. 23 shows illustrations of an exemplary injector system comprising a syringe and a secondary needle and removable needle seal assemblies, per some embodiments herein.
Figure 24:
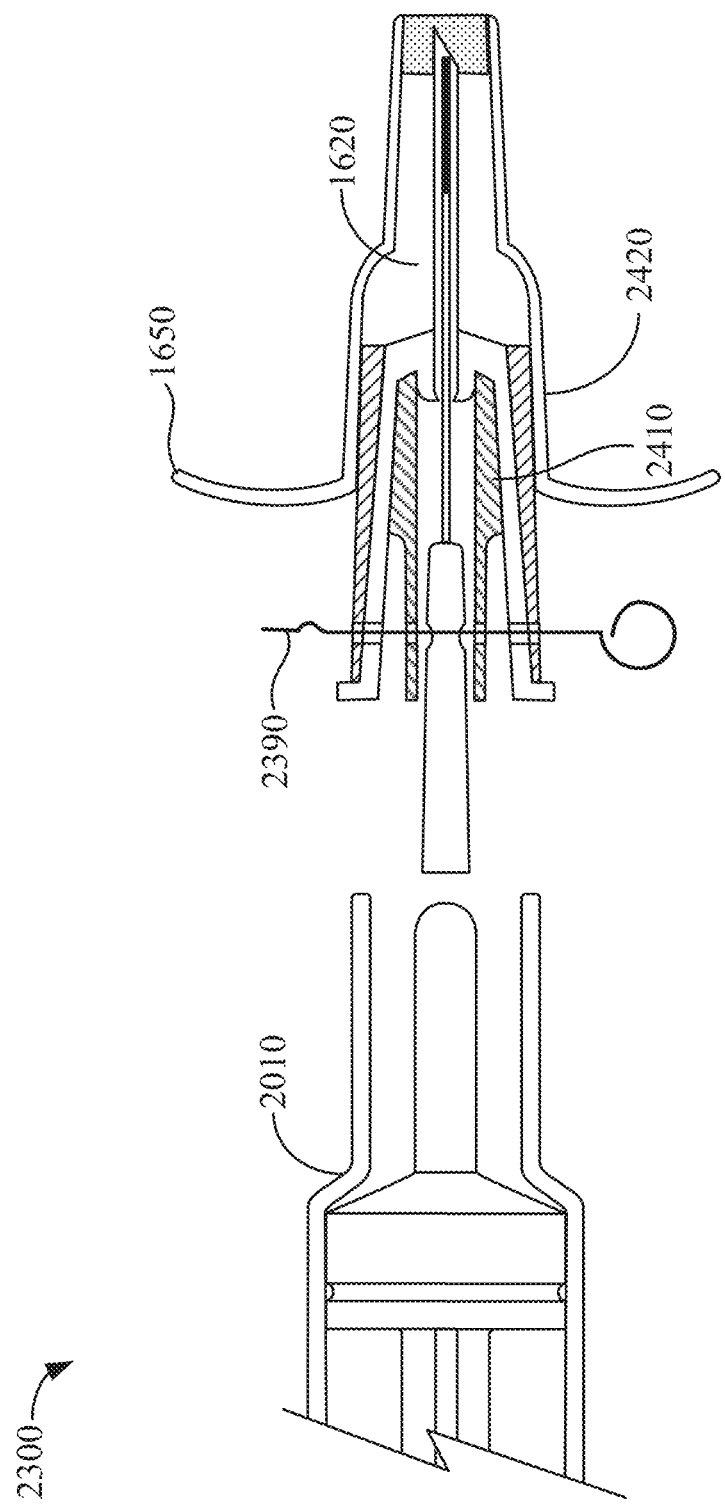
FIG. 24 shows an illustration of an exemplary injector system comprising a syringe and a removable push pin retainer, per some embodiments herein.

FIG. 23 shows an illustration of another exemplary injector system 2300 comprising a latching retainer sheath component 2350 that latches about and on to the syringe 2010. As shown, the latching retainer sheath component 2350 couples to the syringe 2010 by a flexure and a clip. Alternatively, in some embodiments, the latching retainer sheath component 2350 couples to the syringe 2010 by a hinge, a screw, a nut, a slide, a clamp, a bolt, a tie, or any combination thereof. Further, per FIGS. 23 and 24, in some embodiments, the exemplary injector system 2300 further comprises a removable push pin retainer 2390 that prevents movement of the latching retainer sheath component 2350 with respect to the needle 1620, when engaged. In some embodiments, the removable push pin retainer 2390 removably couples the latching retainer sheath component 2350 to a side wall of the needle 1620. In some embodiments, the removable push pin retainer 2390 comprises a pin, a tie, a clip, a flexure, a switch, or any combination thereof. Further, per FIG. 24, in some embodiments, the exemplary injector system 2300 further a commercially available syringe, comprising a distal plunger protrusion that advances the push pin 1690 and an anti-buckling constraint 2410 that constrains the proximal push pin head within a linear path at a fixed angle parallel to the needle lumen axis. The anti-buckling constraint 2410 prevents the push pin 1690 from buckling during plunger, push wire, and implant advancement. In some embodiments, the sheath interface 2420 enables easier insertion of the sheath 1650 over the needle 1620 and linear retraction of the sheath over the needle.

Figure 25:
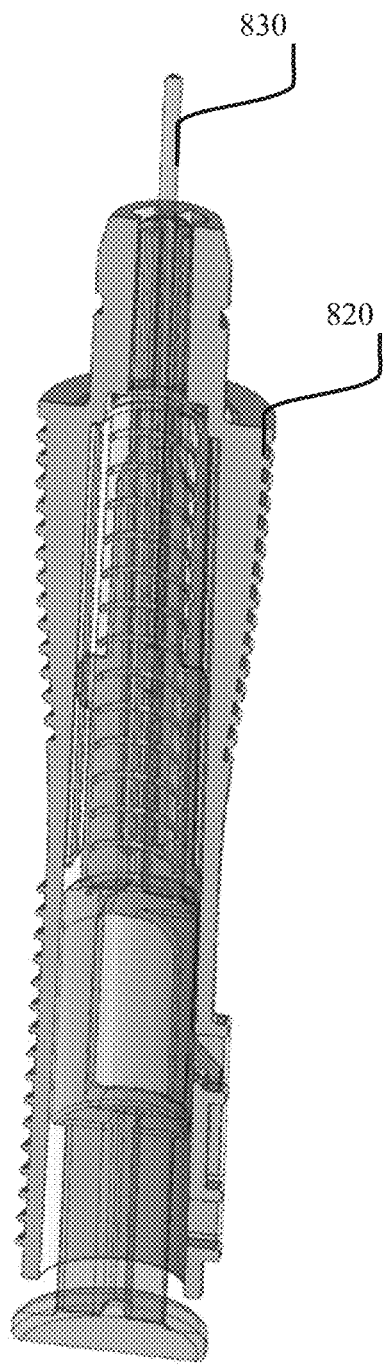
FIG. 25 shows a perspective cross-sectioned illustration of an exemplary third injector system, per some embodiments herein.
Figure 26:
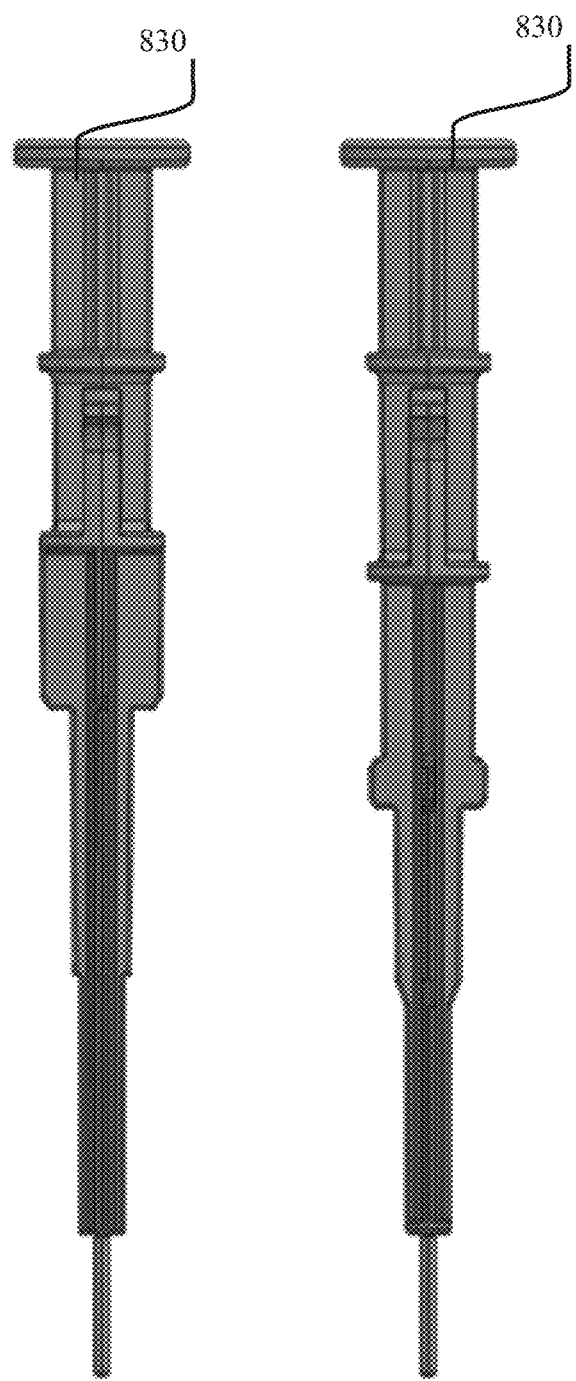
FIG. 26 shows front view illustrations of exemplary plungers of the third injector system, per some embodiments herein.
Figure 27:
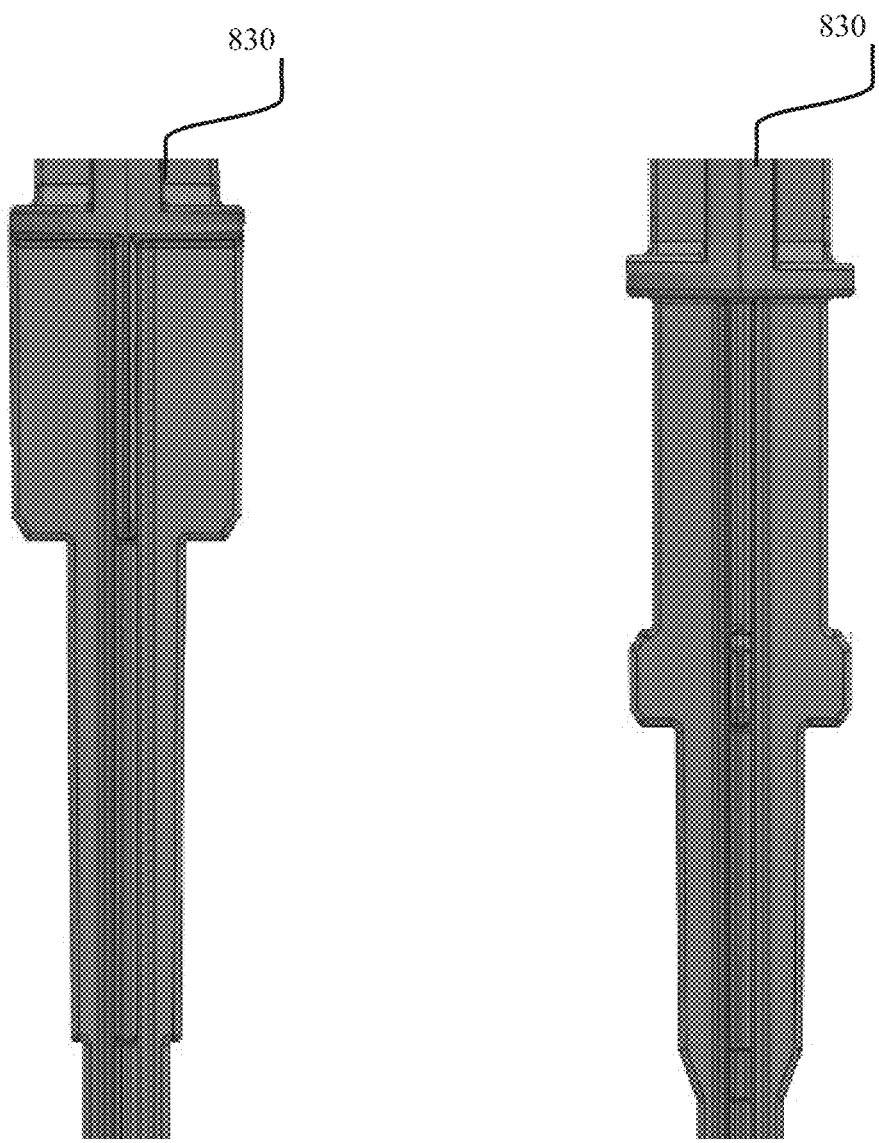
FIG. 27 shows a first set detailed front view illustrations of exemplary plungers of the third injector system, per some embodiments herein.
Figure 28:
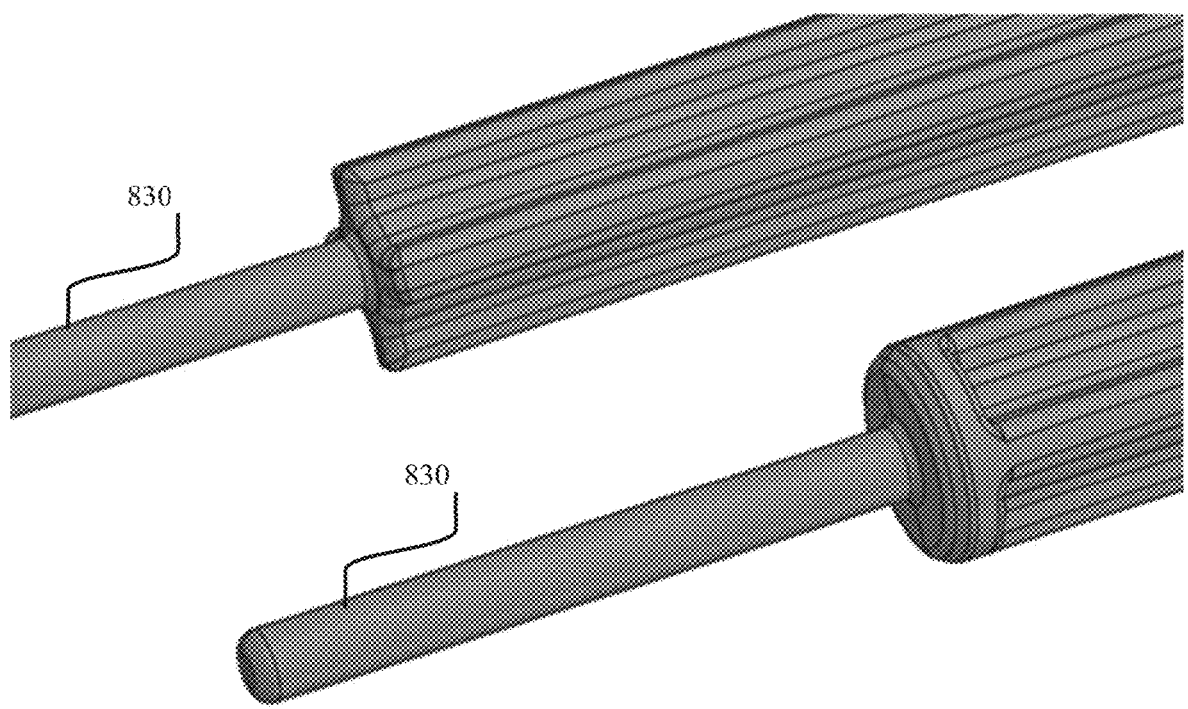
FIG. 28 shows a second set detailed front view illustrations of exemplary plungers of the third injector system, per some embodiments herein.
Figure 29:
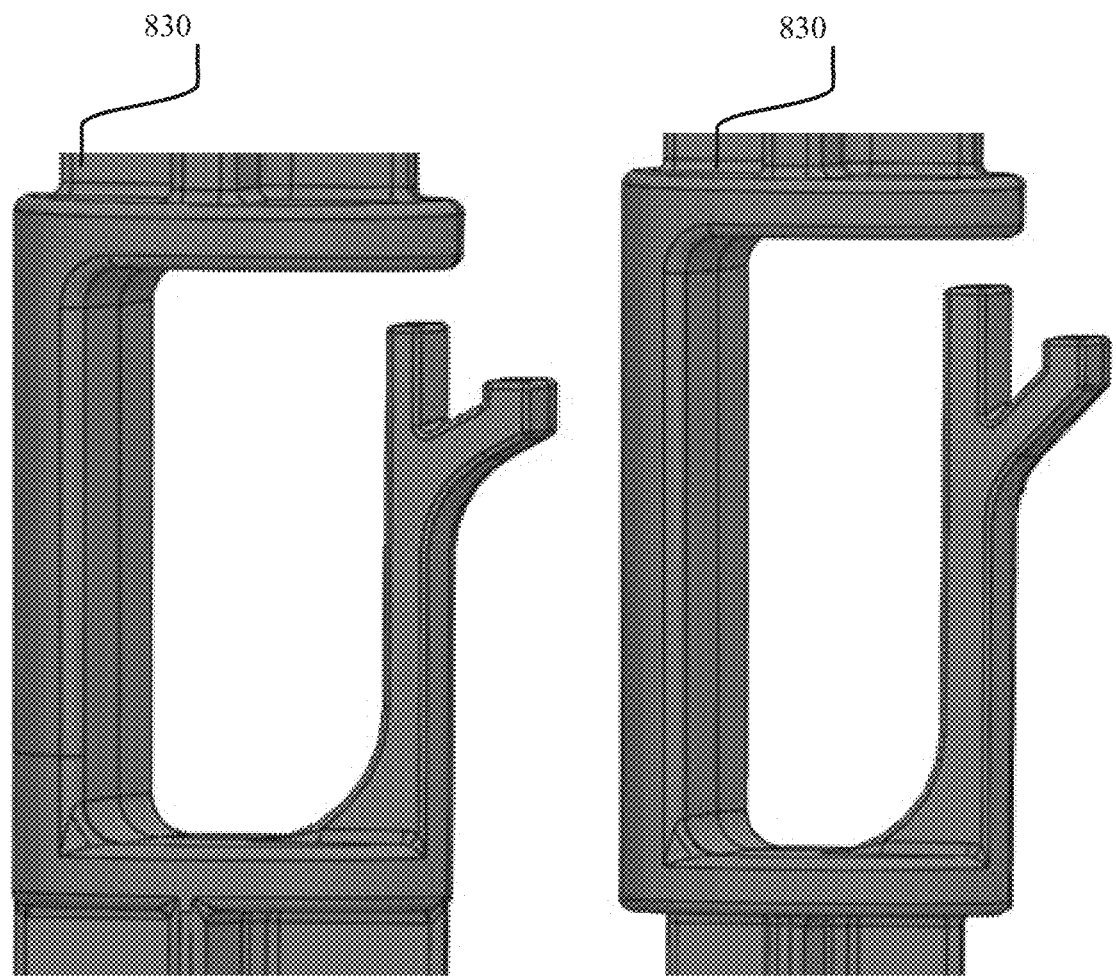
FIG. 29 shows a third set detailed front view illustrations of exemplary plungers of the third injector system, per some embodiments herein.
Figure 30:
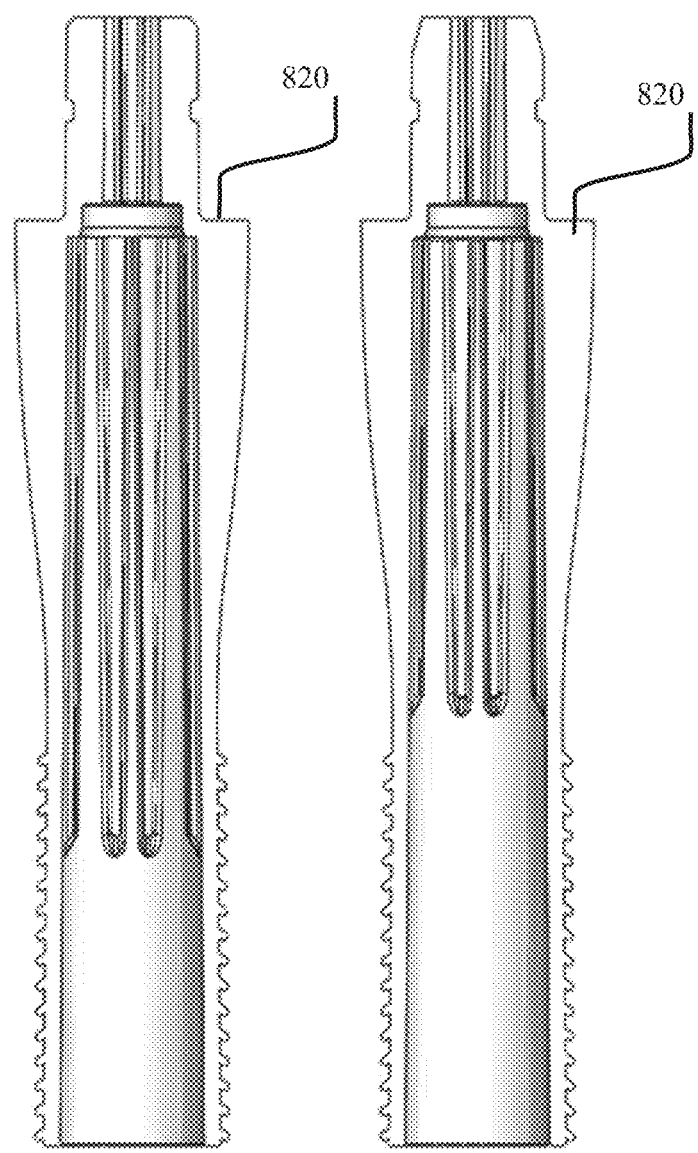
FIG. 30 shows front cross-sectioned view illustrations of an exemplary plunger housing of the third injector system, per some embodiments herein.
Figure 31:
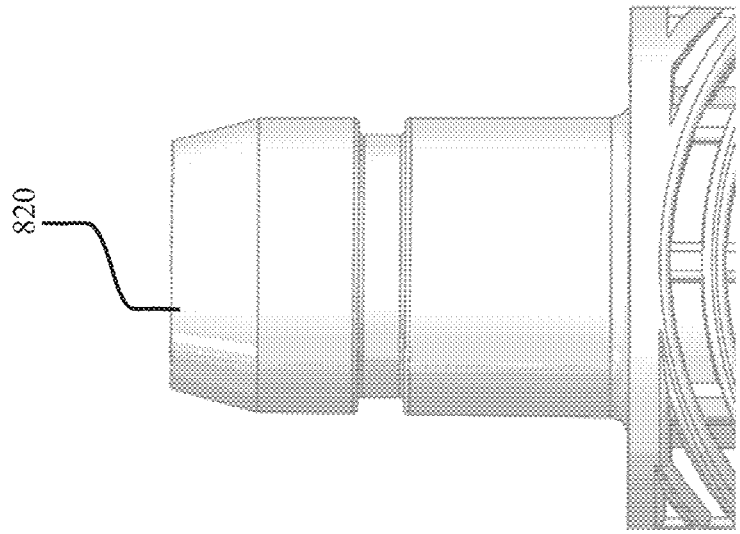
FIG. 31 shows detailed front cross-sectioned view illustrations of an exemplary plunger housing of the third injector system, per some embodiments herein.
Figure 31:
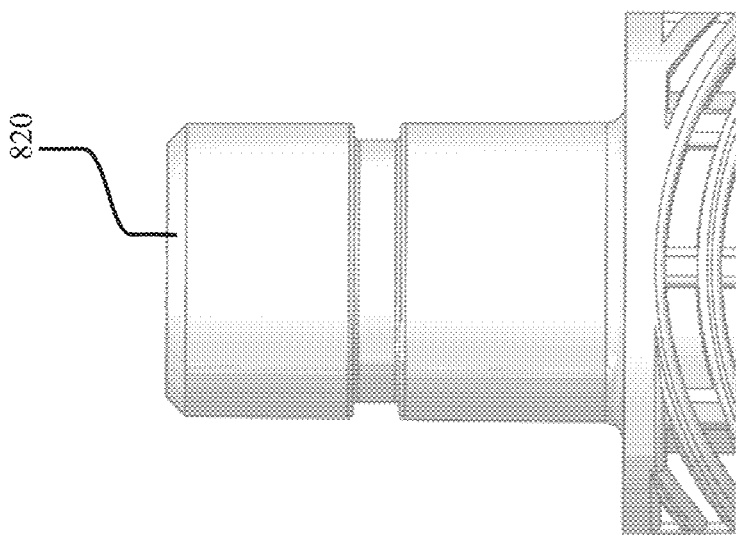

FIG. 25 shows a perspective cross-sectioned illustration of an exemplary third injector system. As seen therein, in some embodiments, an outer surface of the plunger housing has a surface treatment to improve grip. FIGS. 26-29 show front view illustrations of exemplary plungers of the third injector system. FIGS. 30-31 show front cross-sectioned view illustrations of an exemplary plunger housing of the third injector system.

Methods of Injecting an Implant Into an Eye of a Patient

Another aspect provided herein is a method for injecting an implant into an eye of a patient, wherein the method comprises: providing an injector system and injecting the implant into the eye of the patient.

In some embodiments, the system for injecting an implant into an eye of a patient has an unsheathed state and a sheathed state. In some embodiments, the system for injecting an implant into an eye of a patient comprises a needle assembly and a plunger assembly removably coupled to the needle assembly. In some embodiments, the needle assembly comprises a needle housing, a needle, and a needle lumen, the implant inside the needle lumen, and a push pin at least partially disposed within the needle lumen. In some embodiments, the plunger assembly comprises: a plunger housing and a plunger slidably disposed within the plunger housing.

In some embodiments, injecting the implant into the eye of the patient comprises translating the plunger within the plunger housing to engage the push pin and translate the push pin within the needle such that a distal surface of the needle contacts the implant and translates the implant out of the needle and into the eye of the patient.

EXAMPLES

The following illustrative examples are representative of embodiments of the devices and methods described herein and are not meant to be limiting in any way. In one example, the needle housing is received with the implant within the needle. A technician or medical practitioner then attaches the needle housing to the plunger assembly. During operation, the medical practitioner unsheathes the needle assembly and inserts the needle into the eye of the patient until the distal portion of the needle sheath abuts against the eye of the patient. The technician then applies a distal force to the plunger to decouple the first stop feature from the primary second stop feature. The distal force distally translates the plunger such that distal portion of the plunger distally translates the push pin, which translates the implant within the needle into the eye of the patient. Once the first stop feature is decoupled from and distal to the secondary stop feature, the distal force is released, wherein the push pin retracts proximally, and the first stop feature couples to the secondary stop feature. The medical practitioner then removes the needle from the eye of the patient.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

Terms and Definitions

Unless otherwise defined, all technical terms used herein have the same meaning as commonly understood by one of ordinary skill in the art to which this disclosure belongs.

As used herein, the term "biopsy punch" refers to a sharp, hollow, circular instrument for extracting a round piece of tissue.

As used herein, the term "proximal" refers to a direction towards the user of the device and away from the patient.

As used herein, the term "distal" refers to a direction away from the user of the device and towards the patient.

As used herein, the term "lumen" refers to the hollow portion of a needle in which a medicament is transferred.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "about" in reference to a percentage refers to an amount that is greater or less the stated percentage by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. An injector system for injecting an implant into an eye of a patient having an unsheathed state and a sheathed state, the system comprising:
   (a) a needle assembly comprising:
      (i) a needle housing having a proximal end and a distal end;
      (ii) a needle having a proximal end attached to the distal end of the needle housing or within the needle housing, a distal end extending beyond the distal end of the needle housing, and a needle lumen at the distal end of the needle;
      (iii) the needle lumen being configured to receive an implant positioned therewithin;
      (iv) a needle sheath having a seal, wherein the distal end of the needle lumen is within and sealed by the needle seal when the system is in the sheathed state, and wherein the distal end of the needle extends beyond the needle seal when the system is in the unsheathed state; and
      (v) a push pin having a head and a push rod, wherein a distal end of the push rod is disposed within the needle lumen, and wherein translating the push pin in a distal direction ejects the implant from the needle lumen and into the eye of the patient;
      (vi) a resilient member disposed within the needle housing, wherein the resilient member proximally biases the push pin, and
   (b) a plunger assembly comprising:
      (i) a plunger housing; and
      (ii) a plunger slidably disposed within the plunger housing, wherein a distal end of the plunger is engaged with the push pin of the needle assembly when in a distal position within the plunger housing, wherein the injector system comprises only one plunger.

2. The injector system of claim 1, wherein the distal end of the plunger engages the head of the push pin.

3. The injector system of claim 1, wherein the plunger is manually actuated to translate distally within the plunger housing.

4. The injector system of claim 1, wherein a proximal end of the plunger assembly protrudes beyond the plunger housing.

5. The injector system of claim 1, wherein the plunger is mechanically actuated to translate distally within the plunger housing.

6. The injector system of claim 1, wherein the plunger assembly further comprises a compression spring biasing the plunger towards a proximal end of the plunger housing.

7. The injector system of claim 6, wherein the compression spring has a distal end connected to the plunger housing and a proximal end connected to the plunger.

8. The injector system of claim 1, wherein the plunger comprises a first stop feature, wherein the plunger housing comprises a second stop feature engageable with the first stop feature.

9. The injector system of claim 8, wherein the second stop feature comprises a primary second stop and a secondary second stop.

10. The injector system of claim 1, wherein the needle sheath has a proximal portion surrounding the distal end of the needle housing and a distal portion surrounding the distal end of the needle.

11. The injector system of claim 10, wherein the needle sheath is removable from the needle housing by translating in a distal direction away from the needle housing to expose the needle.

12. The injector system of claim 10, wherein the needle sheath translates proximally to the unsheathed state where the distal end of the needle extends beyond the distal portion of the needle sheath.

13. The injector system of claim 1, wherein the needle seal is at the distal end of the needle and seals the distal end of the needle lumen.

14. The injector system of claim 13, wherein the needle seal is within a distal portion of the needle sheath.

15. The injector system of claim 13, wherein the needle sheath is configured to be translated in a proximal direction to cause the needle sheath to completely penetrate the needle seal to expose the needle.

16. The injector system of claim 13, wherein the needle has a length such that the distal end of the needle is within the needle seal when the system is in the sheathed state.

17. The injector system of claim 10, wherein the proximal portion of the needle sheath provides an airtight seal against the needle housing.

18. The injector system of claim 1, further comprising the implant in the needle lumen between the push pin and the seal.

19. An injector system for injecting an implant into an eye of a patient having an unsheathed state and a sheathed state, the system comprising:
   (a) a needle assembly comprising:
      (i) a needle housing having a proximal end and a distal end;
      (ii) a needle having a proximal end attached to the distal end of the needle housing or within the needle housing, a distal end extending beyond the distal end of the needle housing, and a needle lumen at the distal end of the needle;
      (iii) the needle lumen being configured to receive an implant positioned therewithin;
      (iv) a push pin having a head and a push rod, wherein a distal end of the push rod is disposed within the needle lumen, and wherein translating the push pin in a distal direction ejects the implant from the needle lumen and into the eye of the patient;
      (v) a resilient member disposed within the needle housing, wherein the resilient member proximally biases the push pin, and
   (b) a plunger assembly comprising:
      (i) a plunger housing; and
      (ii) a plunger slidably disposed within the plunger housing, wherein a distal end of the plunger is engaged with the push pin of the needle assembly when in a distal position within the plunger housing, wherein the injector system comprises only one plunger.

20. The injector system of claim 19, wherein the distal end of the plunger engages the head of the push pin.

* * * * *